(12) United States Patent
Li et al.

(10) Patent No.: US 11,676,020 B2
(45) Date of Patent: Jun. 13, 2023

(54) SECURE GENOMIC DATA ACCESSIONING

(71) Applicant: Helix OpCo, LLC, San Mateo, CA (US)

(72) Inventors: Maya Hao Li, Seattle, WA (US); Tiffany Roshea Williams, San Francisco, CA (US); Alex Hernsdorf, San Francisco, CA (US)

(73) Assignee: Helix OpCo, LLC, San Mateo, CA (US)

( * ) Notice: Subject to any disclaimer, the term of this patent is extended or adjusted under 35 U.S.C. 154(b) by 0 days.

(21) Appl. No.: 17/678,733

(22) Filed: Feb. 23, 2022

(65) Prior Publication Data

US 2022/0180496 A1  Jun. 9, 2022

Related U.S. Application Data

(63) Continuation of application No. 16/151,167, filed on Oct. 3, 2018, now Pat. No. 11,270,422.

(51) Int. Cl.
| | |
|---|---|
| *G06N 3/08* | (2023.01) |
| *G06T 7/00* | (2017.01) |
| *G06N 5/046* | (2023.01) |
| *G16B 20/00* | (2019.01) |
| *G16B 40/00* | (2019.01) |
| *G16B 50/00* | (2019.01) |

(Continued)

(52) U.S. Cl.
CPC .............. *G06N 3/08* (2013.01); *G06N 5/046* (2013.01); *G06T 7/0002* (2013.01); *G06V 10/764* (2022.01); *G06V 10/82* (2022.01); *G06V 20/62* (2022.01); *G06V 20/80* (2022.01); *G16B 20/00* (2019.02); *G16B 40/00* (2019.02); *G16B 50/00* (2019.02); *G06T 2200/24* (2013.01); *G06T 2207/20084* (2013.01)

(58) Field of Classification Search
CPC combination set(s) only.
See application file for complete search history.

(56) References Cited

U.S. PATENT DOCUMENTS

| | | |
|---|---|---|
| 6,084,590 A | 7/2000 | Robotham et al. |
| 6,144,848 A | 11/2000 | Walsh et al. |

(Continued)

FOREIGN PATENT DOCUMENTS

| | | | |
|---|---|---|---|
| CN | 106203571 A | 12/2016 | |
| FR | 2867650 | * 9/2005 | ........... G06Q 20/326 |

(Continued)

OTHER PUBLICATIONS

"U.S. Appl. No. 16/151,167, Final Office Action dated Aug. 9, 2021", 7 pgs.

(Continued)

*Primary Examiner* — Zhiyu Lu
(74) *Attorney, Agent, or Firm* — Schwegman Lundberg & Woessner, P.A.

(57) ABSTRACT

A biological sample system that efficiently images and registers codes corresponding to biological samples depicted in an image. The biological sample system can implement a neural network to detect the codes individually, and further translate each code into an item identifier. The item identifiers are correlated with network server accounts and a user interface can depict the biological samples with data indicating their registration state.

20 Claims, 18 Drawing Sheets

(51) Int. Cl.
*G06V 20/80* (2022.01)
*G06V 10/764* (2022.01)
*G06V 10/82* (2022.01)
*G06V 20/62* (2022.01)

(56) References Cited

U.S. PATENT DOCUMENTS

| | | | |
|---|---|---|---|
| 7,380,213 B2 | 5/2008 | Pokorny et al. | |
| 8,469,270 B1* | 6/2013 | Rothschild | G06Q 30/02 |
| | | | 705/28 |
| 8,746,560 B2* | 6/2014 | Rothschild | G06F 16/335 |
| | | | 705/28 |
| 9,177,225 B1 | 11/2015 | Cordova-Diba et al. | |
| 9,542,746 B2 | 1/2017 | Wu et al. | |
| 10,002,344 B2 | 6/2018 | Wu et al. | |
| 10,019,803 B2 | 7/2018 | Venable et al. | |
| 10,176,452 B2 | 1/2019 | Rizzolo et al. | |
| 10,210,603 B2 | 2/2019 | Venable et al. | |
| 10,255,302 B1 | 4/2019 | Cosic | |
| 10,289,990 B2 | 5/2019 | Rizzolo et al. | |
| 10,452,897 B1 | 10/2019 | Benkreira et al. | |
| 10,453,046 B2 | 10/2019 | Wu et al. | |
| 10,600,101 B2* | 3/2020 | Rothschild | G06F 3/167 |
| 11,270,422 B2 | 3/2022 | Li et al. | |
| 2003/0212577 A1* | 11/2003 | Nichtberger | G06Q 40/08 |
| | | | 705/2 |
| 2004/0172283 A1* | 9/2004 | Vanderveen | G16H 20/10 |
| | | | 705/2 |
| 2004/0218045 A1 | 11/2004 | Bodnar et al. | |
| 2005/0288571 A1* | 12/2005 | Perkins | A61B 5/742 |
| | | | 600/407 |
| 2007/0067248 A1 | 3/2007 | Chatte | |
| 2008/0041950 A1 | 2/2008 | Michels | |
| 2011/0178927 A1 | 7/2011 | Lindelsee et al. | |
| 2013/0001741 A1 | 7/2013 | Seymour et al. | |
| 2013/0277424 A1* | 10/2013 | Rothschild | G06F 16/951 |
| | | | 235/375 |
| 2014/0091985 A1 | 4/2014 | Birch et al. | |
| 2015/0363625 A1 | 12/2015 | Wu et al. | |
| 2017/0293788 A1 | 10/2017 | Taira et al. | |
| 2018/0205725 A1 | 7/2018 | Cronkright et al. | |
| 2018/0225738 A1* | 8/2018 | Rothschild | G06Q 30/0277 |
| 2018/0341747 A1 | 11/2018 | Bernard et al. | |
| 2018/0343495 A1 | 11/2018 | Loheide et al. | |
| 2019/0286895 A1 | 9/2019 | Zakharov et al. | |
| 2019/0384954 A1 | 12/2019 | Lyubimov et al. | |
| 2020/0111200 A1 | 4/2020 | Li et al. | |

FOREIGN PATENT DOCUMENTS

| | | | | |
|---|---|---|---|---|
| JP | 2005284855 | * | 10/2005 | G06F 17/60 |
| JP | 2014099176 | * | 5/2014 | G06K 7/00 |
| JP | 2019082871 | * | 5/2019 | G06F 3/0482 |
| WO | WO2011000944 | * | 6/2011 | G01N 35/00 |

OTHER PUBLICATIONS

"U.S. Appl. No. 16/151,167, Non Final Office Action dated Feb. 2, 2021", 10 pgs.
"U.S. Appl. No. 16/151,167, Notice of Allowance dated Oct. 28, 2021", 9 pgs.
"U.S. Appl. No. 16/151,167, Response filed Jan. 26, 2021 to Restriction Requirement dated Jan. 11, 2021", 8 pgs.
"U.S. Appl. No. 16/151,167, Response filed Jul. 29, 2021 to Non Final Office Action dated Feb. 2, 2021", 12 pgs.
"U.S. Appl. No. 16/151,167, Response filed Oct. 11, 2021 to Final Office Action dated Aug. 9, 2021", 9 pgs.
"U.S. Appl. No. 16/151,167, Restriction Requirement dated Jan. 11, 2021", 5 pgs.

\* cited by examiner

SECURE GENOMIC DATA ACCESSIONING

CROSS-REFERENCE TO RELATED APPLICATIONS

This application is a continuation of prior application Ser. No. 16/151,167, filed on Oct. 3, 2018, which is incorporated by reference herein in its entirety.

FIELD

The present disclosure relates generally to genomic data storage and, in particular, to special-purpose machines and improvements to such special-purpose machines, and to the technologies by which such special-purpose machines are technically improved to generate genomic user interfaces for securely accessioning user data.

BACKGROUND

Users now have access to genomic tests and services that were recently available only through leading research organizations and clinical laboratories. The decreasing cost of genome sequencing has been one factor in increasing the availability of direct-to-user genomic services. Such genomic services can now quickly complete laboratory analysis of a user's genetic data (e.g., deoxyribonucleic acid (DNA)), and give the user access to the newly generated genetic data. While welcomed by some, these breakthrough advances have nevertheless created several significant technological challenges due to the size, complexity, and nature of genetic data. One challenge includes securely managing biological user data in a network environment in an efficient manner.

BRIEF DESCRIPTION OF THE FIGURES

The inventive subject matter is more fully appreciated in connection with the following detailed description taken in conjunction with the accompanying drawings, in which.

Like reference numerals refer to corresponding parts throughout the several views of the drawings.

DETAILED DESCRIPTION

Figure 1:
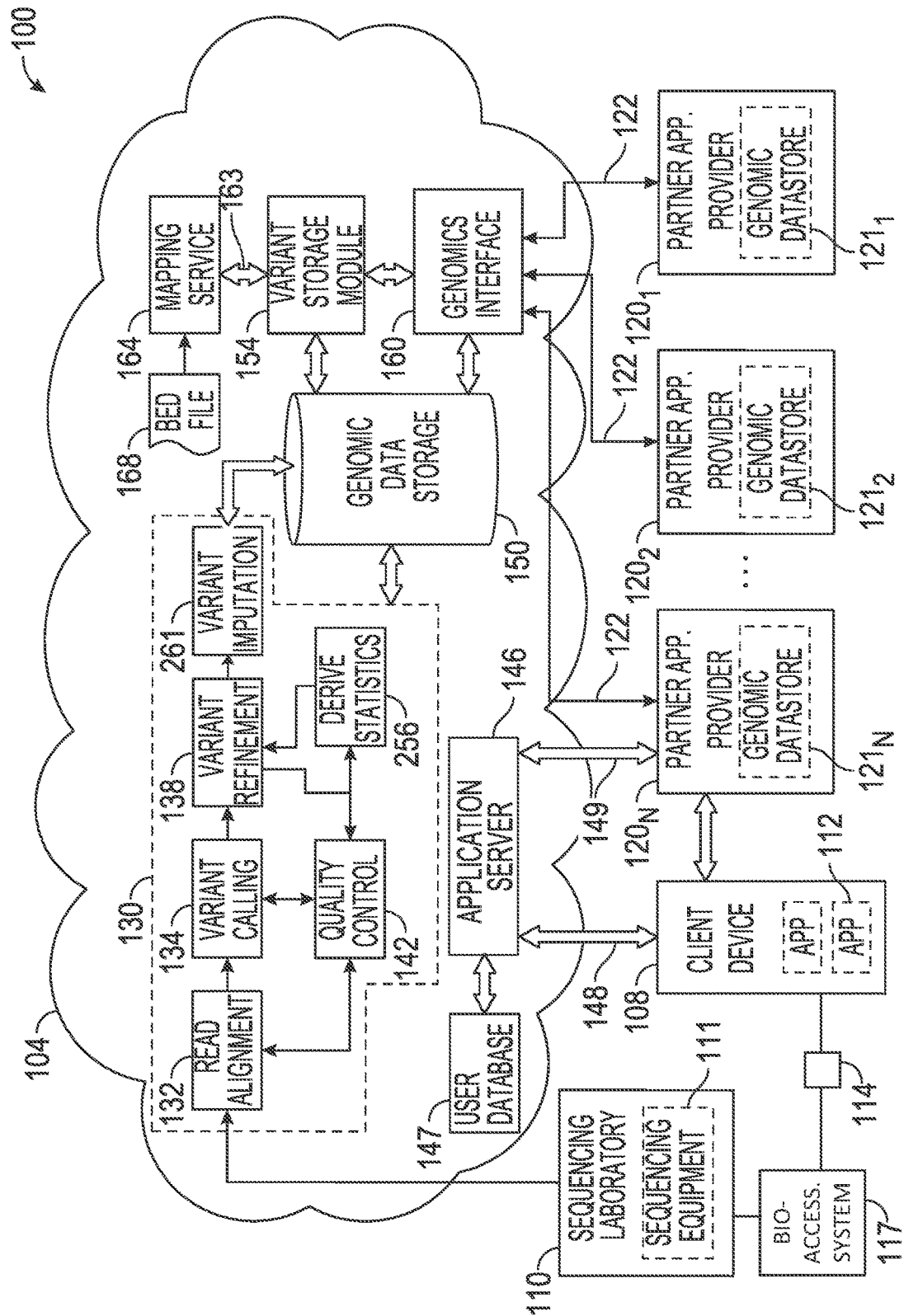
FIG. 1 illustrates a high-level architectural view of a system including a genomic services platform in accordance with the disclosure.

The description that follows discusses systems, methods, techniques, instruction sequences, and computing machine program products that illustrate examples of the present subject matter. For the purposes of explanation, numerous specific details are set forth in order to provide an understanding of various example embodiments of the present subject matter. It will be evident, however, to those skilled in the art, that example embodiments of the present subject matter may be practiced without these specific details.

As mentioned above, it can be difficult to securely and efficiently manage biological user data in a network environment. An example of a network-based genomic service can include a mobile application designed to communicate personalized genetic information based on a user's sequenced data (e.g., genetic variation data). Multiple genomic network services can be utilized to provide the genetic information to the mobile application. However, the different network devices may be located at different geographical locations and operate on different private networks. The different network devices may have different access privileges and security protocols but must nonetheless function in concert to provide the end-user with advanced and personalized network-based genomic services. One bottleneck can arise in accessioning end-users into the genomic network environment, i.e., registering a user with a network account (e.g., a user account), correlating network account data with biological sample data (e.g., saliva sample), performing quality analysis, sequencing the biological sample, and storing the biological sample for later processing (e.g., re-sequencing) in a way that maintains the user's privacy across multiple devices in the network.

To this end, one example of the present disclosure includes a bio-accessioning system is configured to generate an image of one or more user biological items (e.g., saliva containers) that have scannable codes (e.g., barcodes, QR codes). In some example embodiments, the image is parsed to identify regions of interest (ROIs), each of which includes a scannable code. The ROIs can be used to generate a plurality of separate image files, each depicting a biological item and scannable code (e.g., tiles). In some example embodiments, the coordinates of each ROI are stored in a file or as image metadata, which can be used to locate a given ROI within the original image without creating separate image tiles. Each of the scannable codes can be translated to generate an item identifier (e.g., a kitID) that is used to reference a given biological item at one network point (e.g., a networked device at a shipping facility). A lookup can be performed in local memory at the network point or via a remote server request to verify that each of the biological items corresponds to a network account (e.g., a user account) that is managed on another remote server (e.g., a genomic services platform located at a different geographic location on a different network). The bio-accessioning system can further be configured to generate a user interface that displays the biological image with a plurality of visual elements that indicate which of the biological items do not have corresponding network accounts without exposing user-identifying data.

Attention is now directed to FIG. 1, which illustrates a system 100 including a genomic services platform 104 in accordance with the disclosure. As shown, the system 100 includes a sequencing laboratory 110 organized to receive biological samples (e.g., biological sample 114) from users (e.g., saliva from an operator of client device 108). In some example embodiments, the biological samples are received a facility that comprises a bio-accession system 117 that accessions the biological samples, as further discussed below. The accessioned biological samples are then transferred to sequencing laboratory 110 for sequencing and further processing. The sequencing laboratory 110 may include next-generation sequencing (NGS) equipment 111 operative to perform sequencing operations upon the biological samples in order to determine genomic sequence information corresponding to the users. The resulting genomic sequence information may then be provided to the genomic services platform 104 for data processing, data storage, and data access. Such users may possess client device (e.g., client device 108, smartphones, laptop computers) storing software applications (e.g., application 112) downloaded or otherwise obtained from servers operated and provided by partner application providers 120. In one example embodiment, the genomic services platform 104 is operated by an entity having contractual relationships with each of the partner application providers 120 and may provide such providers with selective access to sets of the user genomic information stored by the genomic services platform 104.

In the embodiment of FIG. 1, the genomic services platform 104 may be implemented using "cloud" computing capabilities. As is known, cloud computing may be characterized as a model for facilitating on-demand network access to a shared pool of configurable computing resources (e.g., networks, servers, storage, applications, and services) that can be rapidly provisioned and released with minimal management effort or service provider interaction. Cloud systems can automatically control resources expended by utilizing metering capabilities with respect to, for example, storage, processing, bandwidth, and active user accounts. Various cloud service models are possible, including cloud software as a service (SaaS), cloud platform as a service (PaaS), and cloud infrastructure as a service (IaaS).

In the embodiment of FIG. 1 the genomic services platform 104 may operate on "private" cloud infrastructure provided and managed by one or more third-party organizations. For example, in the embodiment of FIG. 1, the genomic services platform 104 includes a bioinformatics processing network 130 operative in a cloud environment managed by a first third-party organization, with the remainder of the genomic services platform 104 operating on infrastructure (e.g., another subnetwork having a different network address) provided by a second third-party organization. In one embodiment, the bioinformatics processing network 130 operates within the BaseSpace Sequence Hub provided by Illumina, and the remainder of the genomic services platform 104 operates through an Amazon® Web Service (AWS) Cloud. In other embodiments, some or all of the genomic services platform 104 may be implemented using other cloud environments such as, for example, a Microsoft® Azure cloud or another third-party cloud such as DNA Nexus. As shown, the bioinformatics processing network 130 may include a read alignment module 132, a variant calling module 134, a variant refinement module 138, a quality control module 142, and a variant imputation module 261.

In other embodiments, the genomic services platform 104 may be implemented by using on-premise servers and other infrastructure rather than by using cloud-based services. Alternatively, hybrid implementations of the genomic services platform 104 including a combination of on-premise and cloud-based infrastructure are also within the scope of the present disclosure.

Referring again to FIG. 1, the genomics services platform 104 includes an application server 146 that provides a portal through which users may complete a registration process for access to developer applications. In some examples, the application server 146 has access to a customer database, such as user database 147. The user database 147 stores data relating to new and existing users and may be accessed by the application server 146 for user authorization and credentialing purposes, for example. In some examples, and depending on the services requested, there may be a hand-off of user data to facilitate the co-ordination of services between the genomic services platform 104 and other partner application providers 120 (e.g., app developers), other sequencing laboratories 110, or generally between entities within the system 100.

Through a series of API calls 148 to an API endpoint, e.g., Helix™ Application Program Interface (HGAPI), a user's application can invoke certain tasks at the application server 146 to be performed by the application server 146 or in association with other entities within the genomic services platform 104. Typically, tasks using this API will relate to updating user data stored in the user database 147 and may include aspects such as querying data, adding or deleting data, and obtaining metadata about the data. Such applications offered through the portal established by the application server 146 may be the same as, or different from, the applications offered through the partner application providers 120.

Partner application providers 120 can also interact with the application server 146 in relation to non-genomic information. Through a series of API calls 149 to an API endpoint, e.g., Helix™ Partner Application Program Interface (HPAPI), a partner application provider 120 can also invoke certain tasks at the application server 146, such as querying user data, adding or deleting user data, and obtaining metadata about the user data.

Upon completing the registration process, in one embodiment a registered user is sent a receptacle (e.g., a tube or vial) into which the user may deposit a biological sample (e.g., saliva). In one embodiment, the user may receive the receptacle via mail or a package delivery service and may send the receptacle containing the biological sample 114 to the sequencing laboratory 110 using the same or a similar mode of delivery. As part of the registration process, the user may be assigned a unique identifier (such as a unique "user registration ID", a "user ID", a "kitID", or another identifier described further below) that is imprinted or otherwise included on a label attached to the receptacle for the biological sample 114 sent to the user. The user ID may be in the form of a bar code for tracking progress of the user's biological sample through the sequencing laboratory 110 and in identifying the user's biological sample and related information in the bioinformatics processing network 130. The labeling associated with biological sample 114 sent to the sequencing laboratory 110 typically lacks any personal information enabling direct identification of the users associated the biological sample 114.

In one embodiment, a user may register via the portal established by the application server 146 prior to ordering genomic-related applications or network services from partner application providers 120. In other embodiments, the user may access or download an application directly from a partner application provider 120 and provide registration or purchase information that is then forwarded to the genomic services platform 104 via an API endpoint, e.g., HPAPI. Upon receiving the registration information, the operator of the genomic services platform 104 may send a receptacle to the user for receiving a biological sample 114, which is subsequently sent by the user to the sequencing laboratory 110.

Figure 2:
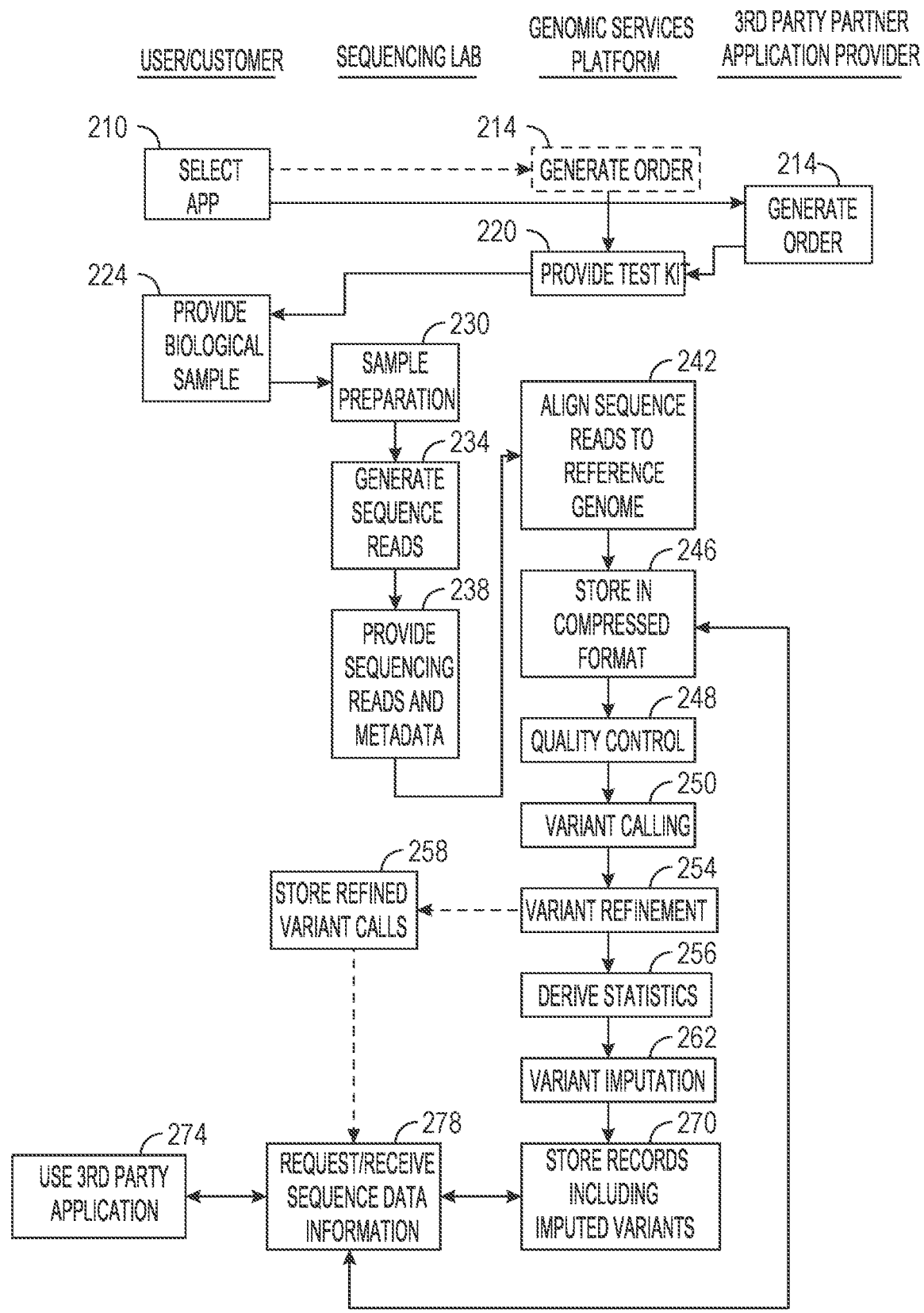
FIG. 2 illustrates an exemplary set of operations performed within the system of FIG. 1.

Attention is now directed to FIG. 2, which illustrates a flow diagram of operations performed within the system 100, according to some example embodiments. As shown, a user may select an application or network service through either the portal provided by the application server 146 or via a website or the like provided by a partner application provider 120 (stage 210). In response, either the application server 146 or the partner application provider 120 may generate an order (stage 214), which causes a test kit including a receptacle for a biological sample 114 to be sent to the user (stage 220). The user then provides the biological sample 114 to the sequencing laboratory 110 (stage 224).

Upon receiving the biological sample 114, the sequencing laboratory 110 prepares the biological sample 114 for sequencing (stage 230). As part of the preparation process, the biological sample 114 may be placed in a sample preparation cartridge to which reagents or other substances are added pursuant to the preparation protocol utilized. Such preparation of the biological sample 114 may include, for example, isolating or purifying the biological sample 114 and performing one or more of cleaving, degrading, annealing, hybridizing, denaturing, or ligating processes involving the biological sample 114. These processes may in some examples occur during transit of the biological sample 114 to the sequencing laboratory 110. Any suitable sample preparation operation known to those of ordinary skill in the art may be employed during stage 230.

Once the biological sample 114 has been prepared, it is processed by sequencing equipment 111 operative to generate observed genomic sequence reads and related quality score information (stage 234). The sequence reads generated may correspond to some or all of the user's genome sequence including, for example, genomic DNA, cDNA, hnRNA, mRNA, rRNA, tRNA, cRNA, and other forms of spliced or modified RNA. In exemplary embodiments, the sequence reads may relate to, for example, somatic, germline, gene expression, and transcriptome sequences.

Figure 3:
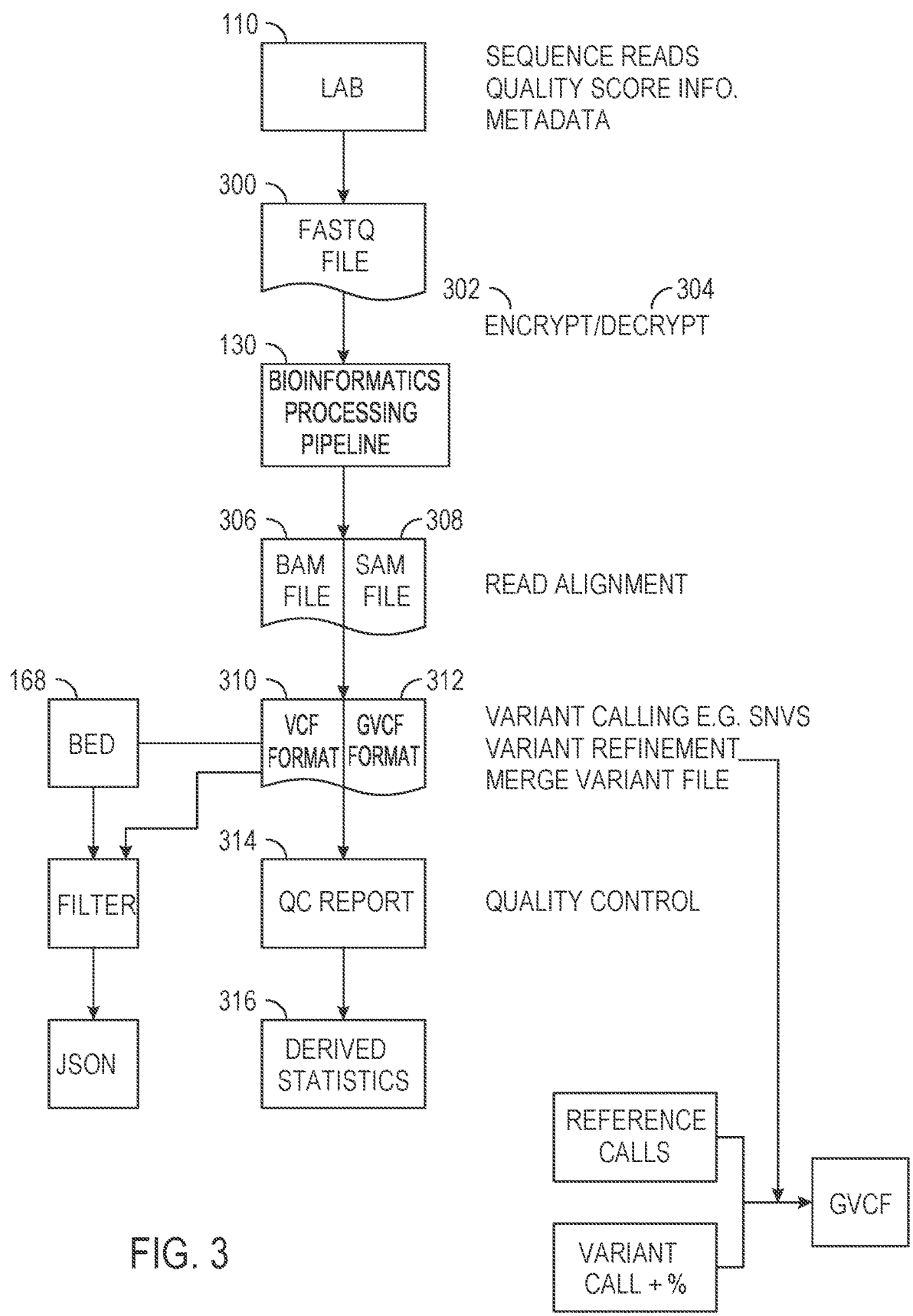
FIG. 3 illustrates an approach for processing sequenced data in different formats, according to some example embodiments.

With reference to FIG. 3, in some example embodiments, related quality score information and certain metadata generated by the sequencing laboratory 110 are included within a storage file 300 (such as a FASTQ file) which is electronically communicated to the bioinformatics processing network 130 (stage 238, FIG. 2). Generally, when sequencing is performed, raw image files are generated that can be used to identify which nucleotide is at a given read area. The FASTQ file format represents the raw read data from the generated images (e.g., 570 megabytes of raw read text data in 7.2 million rows, for a typical user). The FASTQ format can include the sequence string, consisting of the nucleotide sequence of each read, and can also include a quality score for every base. The storage file 300, or simply the raw images of sequence reads and related information, may be encrypted at 302 using one or more conventional techniques prior to being communicated to the bioinformatics processing network 130 and subsequently decrypted at 304. For example, the storage file 300 may be encrypted with a symmetric key, which may itself be encrypted. In some example embodiments, the storage file 300 can be encrypted and transferred using an asymmetric key-pair.

As is discussed below, and with reference to FIG. 2 and FIG. 3, in one embodiment the bioinformatics processing network 130 uses this information from the sequencing laboratory 110 together with population variation data in order to perform the following operations:

1. Read Alignment: align the observed sequence reads in a FASTQ file 300 (e.g., a storage file) to a reference genome, which may be in a non-FASTQ format (e.g., FASTA) and store the alignments in a file in a format such as a Sequence Alignment Map (SAM) file 308 (stage 242, FIG. 2), which, while compressed, can still exceed 1.4 GB with 1.4 million lines of text data. The SAM file 308 can be converted into a Binary Alignment Map (BAM) file 306 (e.g., a 7.5 GB text data file), which is a binary representation of the alignment data in the SAM file 308.

2. Variant Calling: compare the user's genome to the reference genome and identify variants such as a single nucleotide polymorphisms, insertions, and deletions and store these variants in a file format such as a variant call file 310 (VCF format), or genomic variant call file 312 (GVCF format) (stage 250, FIG. 2). The VCF format is a file format for storing DNA variation data such as single-nucleotide variants (SNVs), also called single-nucleotide polymorphisms (SNPs), and other variations, such as insertions/deletions (indels), structural variants, annotations, large structural variants, etc. Like FASTQ, SAM, and BAM files, a user's VCF file is often a very large file (e.g., hundreds of gigabytes of text data) having millions of rows, each row having multiple columns or fields of data. Each row of a VCF file corresponds to a variant at one genomic position or region. A VCF further has multiple columns or tab-delimited fields including, for example, a position column that specifies the start of the variant, a reference allele column of the reference genome, and a nonreference allele column comprising the user's allele value, for example.

3. Variant Refinement: perform additional processing and filtering to derive the final variant calls (stage 254, FIG. 2). In some examples, a ploidy correction is performed during the variant refinement step. Ploidy, in genetics, relates to the number of chromosomes occurring in the nucleus of a cell. A chromosome is a threadlike structure of nucleic acids and protein found in the nucleus of most living cells, carrying genetic information in the form of genes. In normal somatic (body) cells, chromosomes exist in pairs. The condition is called diploidy. During meiosis, the cell produces gametes, or germ cells, each containing half the normal or somatic number of chromosomes. This condition is called haploidy. When two germ cells (e.g., egg and sperm) unite, the diploid condition is restored. Polyploidy refers to cells the nuclei of which have three or more times the number of chromosomes found in haploid cells. Some cells have an abnormal number of chromosomes that is not typical for that organism. In some examples, a ploidy correction is performed by making a sex inference using a heuristic based on the ratio of high-quality reads mapped to chromosome Y divided by those mapped to chromosome X.

4. Quality Control: generate a quality control (QC) report 314 with QC metric values computed on the subject's read alignments and/or variant calls (stage 248, FIG. 2).

5. Derived Statistics: In one embodiment statistics 316 may be derived based upon, for example, sequence reads and/or variant information for use in quality control and process monitoring. In some alternate examples, a ploidy correction could be performed in this stage instead by making a sex inference using a heuristic based on the ratio of high-quality reads mapped to chromosome Y divided by those mapped to chromosome X (stage 256, FIG. 2). In some examples, derived statistics are obtained as part of the quality control stage, such that statistic derivation is not performed as a discrete, subsequent operation.

For each of the observed sequence reads in the FASTQ file, the read alignment module 132 determines a corresponding location in a reference sequence (or finds that no such location can be determined) (stage 242). The read alignment module 132 may utilize a mapping algorithm to compare the sequence of a given read to that of the reference sequence and attempt to locate a potentially unique location in the reference sequence that matches the read.

The results of the sequence alignment operation may be stored in a relatively compressed format such as, for example, in a compressed BAM file 306 (stage 246) or in a file utilizing another compressed storage format. The resulting BAM file 306 may, in one example, be indexed relative to the reference sequence (e.g., a SAM file 308) and analyzed by the quality control module 142 (stage 248). In one embodiment, the variant calling module 134 is configured to process the SAM file 308 in order to identify the existence of variants such as single nucleotide variants (SNVs) relative to the reference sequence (stage 250). The results of the variant calling process may be stored within, for example, one or more VCF files or in other variant call file formats. In one embodiment, the variant calling module 134 produces two variant data files, although in alternative implementations only a single variant data file may be produced. The first variant data file (e.g., GVCF 312) provides general information about all sites in the genome, which include both sites with and without variants (reference calls); the second variant data file (e.g., VCF 310) does not provide information for reference calls. The second variant data file (VCF) provides finalized posterior genotype likelihoods for variants (i.e., for each site at which a variant occurs, it gives the probability that the genotype it assigned to the sample at the site is incorrect). The first variant data file includes genotype likelihoods for variants, but they are not finalized as they may be based on incomplete or low-quality information or genotypes. The sequencing and alignment calling process can create many technical artifacts that can lead to inaccurate results. Using various quality metrics computed for the variants, quality filtering is performed on the second variant data file to remove such artifacts. After filtering, the second variant data file is merged with the first variant data file.

In one embodiment, variant refinement (stage 254) is performed with respect to variant and reference calls produced during stage 250 in order to generate a final variant call output of observed variants. As is discussed below, additional variant calls not directly determined by observed results of the sequencing process may be added during a subsequent variant imputation processing step. In some embodiments, for each biological sample processed during stage 254, the variant refinement module 138 merges the two variant data files generated by the variant calling module 134 for the biological sample 114 into a single variant data file, merges records in the file that represent adjacent reference calls, merges records in the file that represent overlapping variant calls or reference calls, performs ploidy correction using derived statistics (stage 256), and performs variant filtering. By merging the two files produced by the variant calling module 134, the variant refinement module 138 produces a variant data file with reference calls from the first file and variants calls with posterior genotype likelihoods from the second file. In one embodiment, the variant data file will contain two types of records that can be merged: records representing adjacent reference calls and records representing overlapping variant calls or reference calls.

In some examples, the variant data file containing the refined variant calls produced by the variant refinement module 138 is stored within a genomic data storage 150 before variant imputation and may be encrypted using conventional techniques (stage 258). In one embodiment, the genomic data storage 150 is implemented using cloud-based storage such as, for example, Amazon Simple Storage Service (S3), which is available through Amazon Web Services™ (AWS). In general, S3 provides persistent storage for HTTP access to store and retrieve data.

In some examples, haplotype reference data is utilized in the variant imputation operation of stage 262 (FIG. 2). A reference haplotype can indicate what types of variants are found at given chromosome positions in a sequence. So, if a chromosome position is known, and a variant is detected at that position but the nature or type of the variant is not known (or is known but with a low degree of certainty or probability), reference to the known variants on the corresponding haplotype position can help to complete or "boost" (or impute) the missing information. These variant records including refined and imputed variants may then be encrypted using conventional techniques and stored within genomic data storage 150 (stage 270) for controlled access by a user or partner application provider 120 as described below.

In some example embodiments, when a user interacts with an application 112 obtained from a partner application provider 120, the application 112 may make requests to the partner application provider 120 which require the partner application provider 120 to access genomic information stored by the genomic services platform 104 (stage 274). Upon receiving such a request, the partner application provider 120 may issue a request for the relevant information through a genomics interface 160 of the genomic services platform 104 comprised of a network interface and a genomics API (stage 278). Referring again to FIG. 1, through a series of API calls 122 to an API endpoint, e.g., Helix™ Genomics Application Program Interface (HGAPI) at the genomics interface 160, a partner application can invoke certain tasks at the genomics interface 160 such as making requests, querying information, adding, updating or deleting information, and obtaining metadata (tags) about the information.

The various system APIs discussed herein (more specifically, the example APIs described herein as HAPI, HPAPI, and HGAPI), allow a partner application provider 120 to integrate genetics into its applications, products, or services. The genomic services platform 104 supports multiple application providers. The APIs are designed to use consistent resource-oriented URLs as well as HTTP response codes to indicate errors. They also support built-in HTTP features, such as HTTP verbs, for compatibility with the majority of standard HTTP clients. All responses are returned as JSON messages.

Using the APIs, a partner can in some examples access two services based on development needs. Each service has both staging and production endpoints. The two hosted, dedicated services can be invoked to notify a partner application provider of user events and to give the partner access to the relevant genetic information that enables DNA-related features. The first service, for example accessible at the endpoint HPAPI, utilizes the user database 147 and can notify a partner about a user's status, including aspects such as where the user's biological sample 114 is in the sequencing process, if they have registered their DNA collection kit, and whether or not they have consented to share their genetic and personal information with the partner's application.

In some examples, the partner API (HPAPI) acts as an interface between the genomic services platform 104 infrastructure and partner application provider 120 infrastructure. This service can provide certain non-genomic data a partner may need to enable their app to query genomic data and return results back to a user. In other aspects, the partner API service specifically notifies partners about one or more of the following events: a user has purchased an app and is granting permission for that app to access their genomic data, a user has submitted a saliva sample and that sample is being processed in the lab, a user's sample has completed sequencing and QC (Quality Control) and the genomic data is available to query, a user's genomic data has been updated due to an upgrade or a change in the bioinformatics processing network 130, a user has withdrawn consent and/or has funded or removed an app.

Some embodiments of a sample service within the system 100 store and serve sample statuses. With reference to the identifier definitions provided above, an example sample service can perform, for example, the following functions: translation of inbound accessioning events from partner application providers 120 that contain a kitId and a user ID to a sampleId, translation of outbound sample status (e.g., BaseSpace sample status) with a sampleId to be identified with a kitId and a user ID, storage of sample statuses for retrieval, and publishing message queues to HPAPI or directly to partners on sample status updates.

In one example of an account update provided by the first service, a user can agree to share his or her relevant genomic and personal information with a partner application, verify an email address, and register a kit. The registration step can be important as a user purchasing a kit might not be the one submitting it. At the time of purchase, a kit will be sent in the mail and eventually a user will register that kit. Since the purchaser may be a different person than the sample provider, the user who delivers genetic data via the spit tube in a kit is not confirmed until that user registers the kit as their own.

The second service, for example accessible at the endpoint HGAPI, can be used to request the relevant genetic information that enables the partner's DNA-relevant features in its application. Accessing a user's variants (or markers), for example, is typically a primary use of this service. In some examples, a "no-call" is issued when the genomic services platform 104 is unable to make a call that met a minimum quality threshold due to lack of coverage or poor fit of the probabilistic variant calling model. A no-call is characterized by the presence of a specific entry, such as "–1", in the genotype array. In some examples, a "reference" call is issued when the genomic services platform 104 observes, in sufficient quantity and with sufficient quality, only bases matching the reference sequence. A reference call is characterized by the presence of only "0" entries in the genotype array. In some examples, a "variant" call is issued when the genomic services platform 104 observes, in sufficient quantity and with sufficient quality, bases not matching the reference sequence. A variant call is characterized by the presence of any element in the genotype array greater than 0, representing the presence of an alternative allele present in alternate bases. If the record is not a no-call or a reference call, then it is a variant call.

In some examples, an access token (e.g., OAuth access token) is needed any time a partner application calls a system API to read a user's information. When a partner requests an OAuth access token, it is required to define token parameters, such as grant type and scope. A partner will need credential pairs to continue, which can be generated by performing appropriate credentialing steps. All API requests are made over HTTPS. Calls made over plain HTTP will fail. API requests without authentication will also fail.

In some example embodiments, a request for relevant information from a partner application provider 120 includes a unique ID ("PAC ID" or user ID) that identifies a binary tuple of the form (app, user), where app is a value identifying one of the application from the partner application provider 120 (e.g., application 112 on client device 108), and user is a value identifying the particular end-user interacting with the application 112 corresponding to the app. In some examples, the PAC ID may comprise a three-part tuple in the form of (partner, app, user) with corresponding values identifying a partner application provider 120, an application 112, and a user. Other combinations of values are possible, such as (partner, app). Irrespective of which PAC ID is used, an objective of a PAC ID is to allow a partner application provider 120 refer to a user without knowing the actual "value" of the user and to maintain anonymity and privacy in health records. Upon receiving the request including the PAC ID, the genomics interface 160 may present it to the variant storage module 154.

In one embodiment, the variant storage module 154 operates on a server-less framework in a cloud environment, such as Amazon Web Services (AWS Lambda). The AWS Lambda system allows the variant storage module 154 to run code without provisioning or managing servers. The variant storage module 154 accrues costs only for the compute time it consumes when running its functions. There is no charge when the code is not running. This can be important because call volume demands tend to be highly variable. In some examples, the variant storage module 154 receives in excess of one thousand requests per minute for information. The server-less arrangement is highly scalable and minimizes running costs for the variant storage module 154, and indirectly for partners and users. Using AWS Lambda, the variant storage module 154 can run code for virtually any type of partner or user application or backend service with very minimal or zero administration.

In some examples, the variant storage module 154 performs automated tests. The tests are run for any code change that must pass the tests before being deployed to production. For a given PAC ID, the variant storage module 154 may create and output a file and send to HGAPI an expected result that may be investigated if incorrect. In another example, a BED file 168 downloaded from the mapping service 164 is checked for conformity with an expected result. Other automated tests include checking that a request without a user ID (e.g., PAC ID) or app ID, or having a bad PAC ID or app ID, fails. Some data files used within the system 100 may be in a binary variant call format (BCF, or a BAM file described elsewhere herein), and each user may have an associated BCF. Given a BCF, further automated testing may check that filtering by a given region returns correct or expected test intervals, or does not contain a given interval. Other testing may check, again given a BCF file, that an open boundary condition is correctly handled, or that overlapping regions are correctly handled, or that compared to a converted VCF, certain results are expected. Other automated tests may include checking that a BED file can be opened correctly, or that if it cannot be opened correctly, an error message is thrown. Other testing may check for attempts to open non-existent BED files, or to check connectivity with the mapping service 164 such that given an invalid App ID and/or PAC ID, no BED file is returned. Other tests include reference block trimming, for example checking that a returned interval is always a subset of the applicable sequence region, or that a reference block that overlaps multiple regions returns correctly each restricted overlapping region. In some examples, the data used for automated tests is dummy data that mimics what real data will look like in production. In other examples, the test data is derived from real biological samples (cell lines) and modified to be used for testing.

Figure 4:
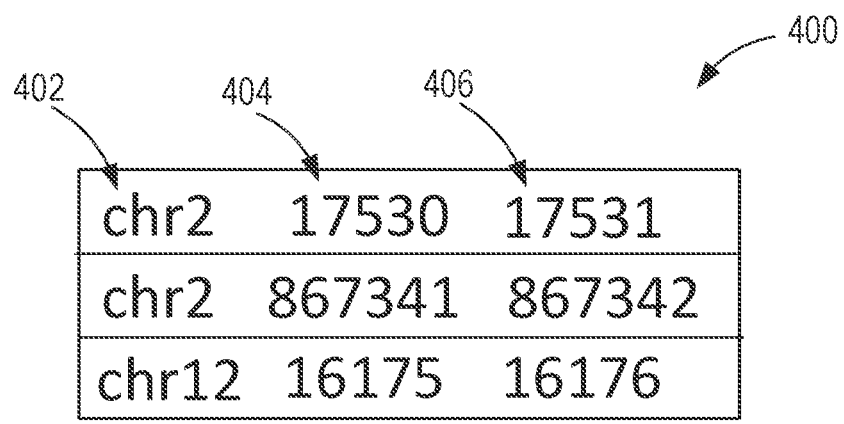
FIG. 4 displays an example Browser Extensible Data (BED) file that defines specific regions of a genome, according to some example embodiments.

FIG. 4 displays an example Browser Extensible Data (BED) file 400 that defines specific regions of a genome. The BED file 400 includes three fields that define: a chromosome 402, a start position 404, and an end position 406 in the genome. Various conventions may be utilized to specify these locations. In some examples, a BED file includes definitions of multiple "DNA windows" defining regions (e.g., one or more ranges of reference locations) of a user genome that may be requested by a particular partner application provider 120 or application 112 through the genomics interface 160.

For example, upon a request for user genomic data from a partner application provider 120 being received via genomics interface 160, the variant storage module 154 then retrieves all the variants pertaining to a user's genome and filters these based upon the PAC ID and the appropriate DNA window specified in the BED file 168. The fetched variants are then returned via a secure connection to the requesting partner application provider 120, and potentially stored by the requesting partner application provider 120 in an optional genomic datastore 121. This enables the partner application provider 120 to deliver corresponding variant data to the application 112 responsible for initiating the request for genomic information in a controlled and secure manner. The content of the corresponding variant data will generally be dependent upon the nature of the application 112. In this way, a user's genetic information can be sequenced once, stored indefinitely, and then queried again, potentially many times, to provide further biogenetic information in a secure manner.

Further details regarding selective access to genomic user data are found in Application Ser. No. 62/535,779, titled "Genomic Services Platform Supporting Multiple Application Providers", filed on Jul. 21, 2017, which is incorporated by reference in its entirety.

Figure 5:
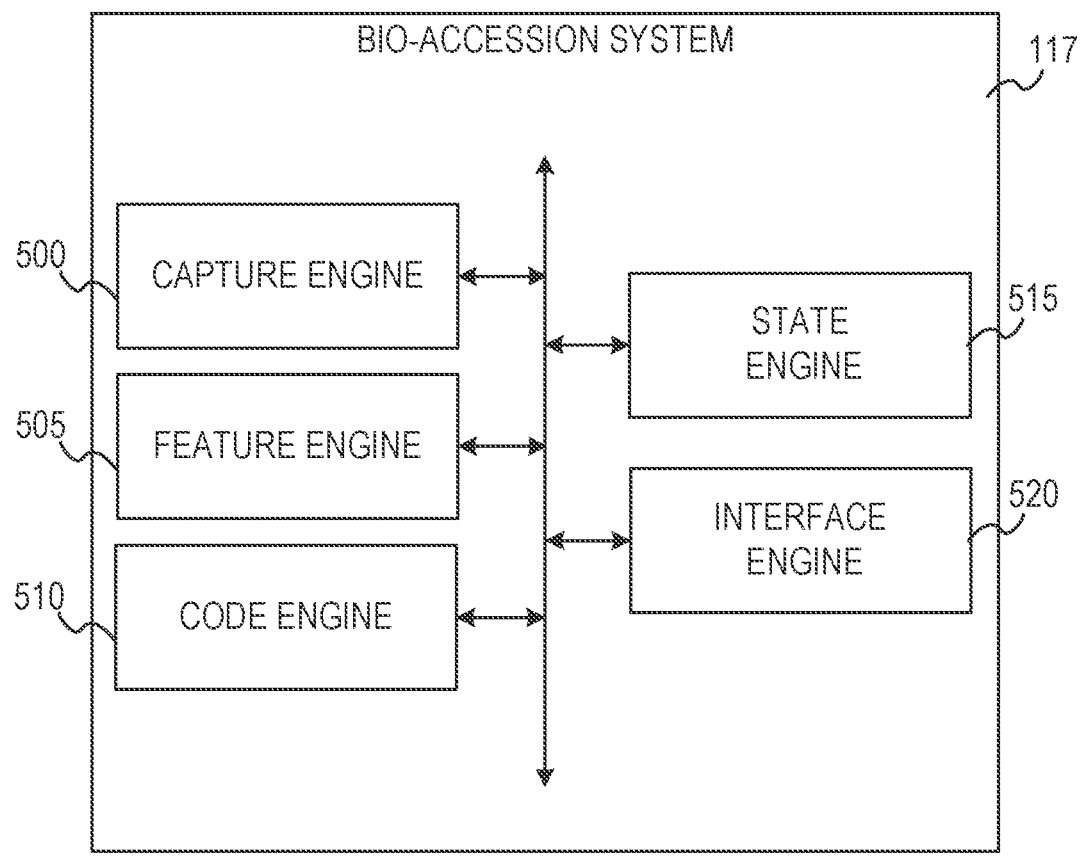
FIG. 5 shows example internal functional engines of a bio-accession system, according to some example embodiments.

Attention is kindly directed to FIG. 5, which shows example internal functional engines of a bio-accession system 117, according to some example embodiments. To avoid obscuring the inventive subject matter with unnecessary detail, various functional components (e.g., modules and engines) that are not germane to conveying an understanding of the inventive subject matter have been omitted from FIG. 5. However, a skilled artisan will readily recognize that various additional functional components may be supported by the bio-accession system 117 to facilitate additional functionality that is not specifically described herein.

As is understood by skilled artisans in the relevant computer arts, each functional component (e.g., engine) illustrated in FIG. 5 may be implemented using hardware (e.g., a processor of a machine) or a combination of logic (e.g., executable software instructions) and hardware (e.g., memory and processor of a machine) for executing the logic. Furthermore, the various functional components depicted in FIG. 5 may reside on a single computer (e.g., a laptop), or may be distributed across several computers in various arrangements such as cloud-based architectures. Moreover, any two or more modules of the bio-accession system 117 may be combined into a single module, or subdivided among multiple modules. It shall be appreciated that while the functional components (e.g., engines) of FIG. 5 are discussed in the singular sense, in other embodiments, multiple instances of one or more of the modules may be employed.

As illustrated, the bio-accession system 117 comprises a capture engine 500, a feature engine 505, a code engine 510, a state engine 515, an interface engine 520, and a visual analysis system 525, according to some example embodiments. The capture engine 500 manages generating images of biological samples (e.g., biological sample containers) using an image sensor, such as a CCD or CMOS sensor. The feature engine 505 is configured to detect image features depicted in images generated by the capture engine 500. In some example embodiments, the feature engine 505 implements a convolutional neural network trained to detect scannable codes, such as barcodes or QR codes. Further, in some example embodiments, the feature engine 505 is configured to perform object recognition of biological container shapes (e.g., vials, cups) that hold biological samples of users, as discussed in further detail below. The feature engine 505 further manages generating a plurality of image tiles, each of which depicts an individual scannable code. In some example embodiments, the feature engine 505 generates the image tiles by cropping the original image multiple times around each detected scannable code. As used here, the initial image is the image that depicts multiple features (e.g., multiple biological containers, multiple scannable codes); whereas the image tile depicts at most one item (e.g., one biological container, one scannable code). In other example embodiments, the feature engine 505 does not generate image tiles that depict individual scannable codes, but rather stores the coordinates of each scannable code as a region of interest (ROI) that specifies where a given scannable code is located within the initial image.

The code engine 510 is configured to translate (e.g., read) scannable codes detected by the feature engine 505 into item identifiers. For example, the code engine 510 can be implemented as a barcode translation scheme that receives an image tile file as an input and generates an item identifier (e.g., a kit ID) as output, where each item identifier corresponds to a different user. In some example embodiments, the code engine 510 can be configured to generate multiple item identifiers from the original image directly. For example, the code engine 510 can receive the ROI coordinate data that specifies where each of the scannable codes is located in the initial image; the code engine 510 can then process each ROI in turn to generate individual item identifiers.

The state engine 515 is configured to determine whether each of the biological items has a corresponding network account on a network platform. For example, the state engine 515 can identify kitIDs generated by the code engine 510, and determine whether each of the item identifiers corresponds to a userID of a user account in the user database 147.

In some example embodiments, the state engine 515 is configured to automatically change the state of received biological samples from "unknown" (e.g., pending, null) to "accessioned" (e.g., received, registered) in response to determining that the item identifiers have corresponding network accounts. In some example embodiments, the state engine 515 performs state changes in a batch operation that automatically transmits the state data to application server 146 for storage in user database 147. State engine 515 can further be configured to initiate one or more user communication messages that cause the application server 146 to contact the client device 108 via electronic message to indicate to the client device 108 that further biological samples are required.

The interface engine 520 is configured to generate an accession user interface that displays a composite image that depicts the plurality of biological items and further indicates which of the plurality of biological items do not have corresponding network accounts, as described in further detail with reference to FIG. 11 below.

Figure 6:
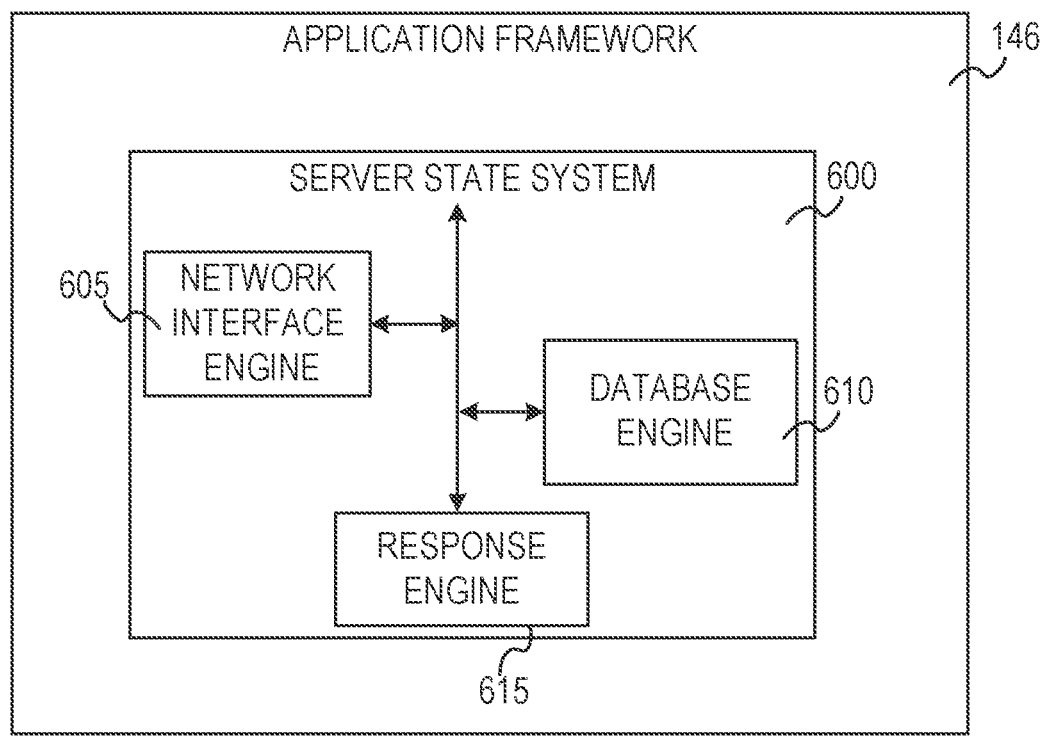
FIG. 6 shows example functional engines of a server state system, according to some example embodiments.

FIG. 6 shows example functional engines of a server state system 600, according to some example embodiments. As illustrated in the example of FIG. 6, the server state system 600 executes from the application server 146 to perform server-side functions for the bio-accession system 117. As illustrated, the server state system 600 comprises a network interface engine 605, a database engine 610, and a response engine 615. The network interface engine 605 is configured as an application program interface (API) that receives validation requests from the state engine 515 on the bio-accession system 117 (FIG. 5). The database engine 610 receives request parameters data including a plurality of item identifiers from the network interface engine 605 and programmatically accesses the user database 147 to determine whether each of the item identifiers has a corresponding network account. In some example embodiments, the user database 147 comprises a lookup table that correlates a given item identifier of a user to the userID of that user. The network interface engine 605 receives, from the database engine 610, results data that indicates which of the item identifiers do not have network accounts from the database engine 610 and transmits the results data to the state engine 515 (FIG. 5) without transmitting the network account identifiers (e.g., user IDs) to the bio-accession system 117. The response engine 615 is configured to perform follow-up operations in response to determining that a given item identifier does not have a corresponding network account. For example, the response engine 615 can be configured as a CRM system that generates an issue ticket and transmits a notification to a client device 108 of a user to notify the user that further biological samples are required or that an issue has occurred with his or her biological sample. In this way, the user can be successfully accessioned without transmitting sensitive data (e.g., a user ID, a user's sequence data) over differently secured networks with different access privileges.

Figure 7:
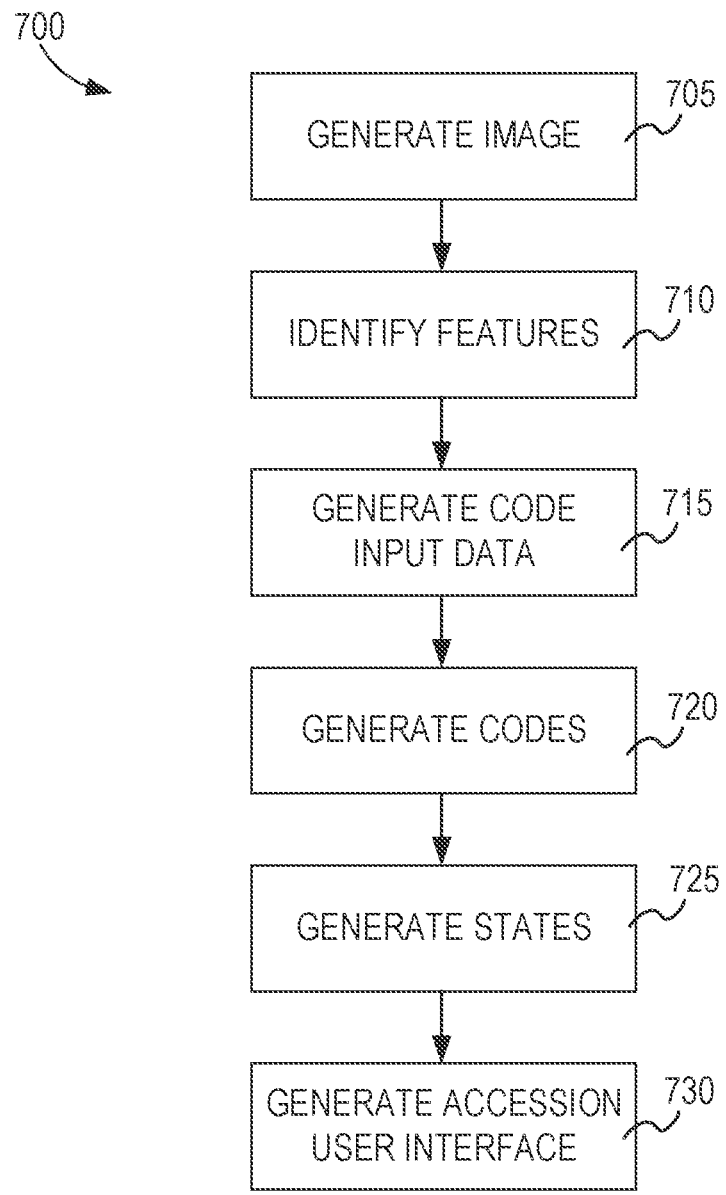
FIG. 7 shows a flow diagram of a method for implementing secure genomic data accessioning, according to some example embodiments.

FIG. 7 shows a flow diagram of a method 700 for implementing secure genomic data accessioning, according to some example embodiments. At operation 705, the capture engine 500 generates an image of one or more biological items. At operation 710, the feature engine 505 identifies a plurality of features of the same type in the image generated at operation 705. For example, at operation 710, the feature engine 505 implements a convolutional neural network that is trained to simultaneously detect multiple barcodes in the image. At operation 715, the feature engine 505 generates scannable code input data for translation. For example, the feature engine 505 generates a plurality of image tiles by cropping the initial image (i.e., the image generated at operation 705) one or more times around each of the detected scannable codes. In some example embodiments, at operation 715, the feature engine 505 generates ROI coordinate data, wherein each set of ROI coordinates specifies an area depicting a scannable code within the original image.

At operation 720, the code engine 510 generates the item identifiers from the code input data using a code translation scheme, such as a bar code reader. In some example embodiments, the code reading scheme processes only individual codes, one at a time, in a serial process. For example, at operation 720, the code engine 510 identifies a directory comprising a plurality of image tiles and applies the code reading scheme to each tile to rapidly generate item identifiers in a serialized process.

In some example embodiments, instead of processing individual files the code reading scheme is directed to different areas of the same image file to process codes. For example, at operation 720, the code engine 510 can receive a set of ROI coordinates within the initial image and apply the code reading scheme to each set of ROI coordinates to generate item identifiers. In some example embodiments, operation 720 is implemented as a parallel process, wherein the code engine 510 processes multiple tiles or ROI coordinates sets concurrently (e.g., multiple threads) or in parallel (e.g., multiple processors, GPU parallelism).

At operation 725, the state engine 515 determines the state of each of the generated item identifiers. For example, at operation 725, the state engine 515 transmits a validation request to a server, wherein the validation request comprises the plurality of item identifiers. At operation 730, the interface engine 520 generates a user interface depicting the plurality of biological items as arranged in the initial image, with additional visual elements that indicate which of the biological items have network accounts and which of the biological items do not have network accounts, as discussed with reference to FIG. 8, below.

Figure 8:
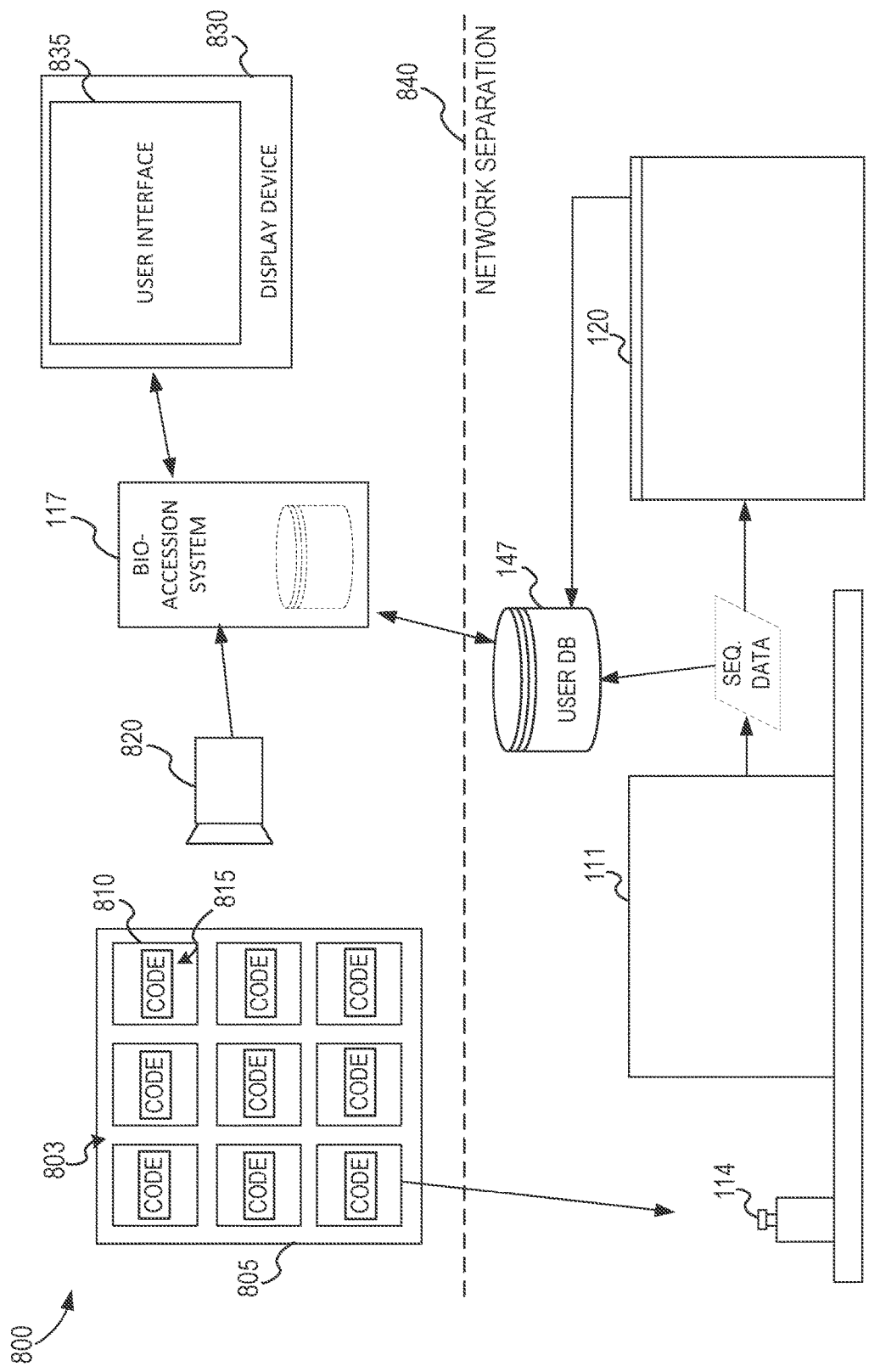
FIG. 8 shows an example network architecture for implementing secure genomic data accessioning, according to some example embodiments.

FIG. 8 shows an example network architecture 800 for implementing secure genomic data accessioning, according to some example embodiments. In the example illustrated in FIG. 8, the network architecture 800 includes a network separation 840, which denotes differently configured networks (e.g., different private networks, a local network and a remote network). For example, the structures above the network separation 840 can be on a first private network from which the bio-accession system 117 operates and the structures below the network separation 840 are on a second private network (e.g., a private network of the sequencing laboratory 110). As part of a batch accessioning approach, multiple biological items received from different users (e.g., vials of saliva of different users) are received and positioned in a rack. An image sensor 820 then generates an image 805 of the plurality of biological items 803. Each of the biological items (e.g., biological item 810) includes a scannable code (e.g., code 815) that can be translated into an item identifier (e.g., a kitID). To facilitate batch imaging, the plurality of biological items 803 can be oriented so that the scannable codes are facing or otherwise visible to the image sensor 820.

After the image sensor 820 generates the image 805 of the plurality of biological items 803, the image 805 is stored in local memory of the bio-accession system 117 or processing. In particular, for example, the bio-accession system 117 can apply a machine learning scheme, such as a convolutional neural network, to identify regions of interest (ROIs) that correspond to the location of the scannable codes within the image 805. In some example embodiments, the machine learning scheme is configured to identify the scannable codes directly. For example, the machine learning scheme can be a convolutional neural network configured to detect barcodes and label coordinates denoting a region of interest around a detected barcode.

After detecting the plurality of scannable codes, the bio-accession system 117 then generates a plurality of image tiles from the image 805. For example, the bio-accession system 117 generates nine tiles from the nine depicted biological items in the image 805. Each of the tiles can be a small image file (e.g., 40 pixel square crops from image 805). The bio-accession system 117 then translates the scannable code to an item identifier (e.g., kit ID). The bio-accession system 117 determines whether each of the item identifiers has a corresponding network account.

For example, the bio-accession system 117 can transmit a request to the user database 147 to determine whether a user account exists for a given item identifier. The bio-accession system 117 then generates an accession user interface 835, which can be displayed on a display device 830. The accession user interface 835 includes a display of a composite image generated from the item tiles. The composite image can include visual elements that indicate which, if any, of the biological items do not have network accounts in the network (e.g., genomics services platform 104, user database 147). An operator (e.g., human administrator, robotic arm) of the bio-accession system 117 may then readily identify the flagged items and physically remove them from the rack so that the associated biological sample does not undergo sequencing. The remaining biological samples are then sequenced, and the resulting genomic sequence information may then be provided to the genomic services platform 104 for data processing, data storage, and data access. Further, users may use the client device 108 to access software application (e.g., application 112) provided by partner application providers 120 to interact with their sequenced data, as discussed above.

Figure 9B:
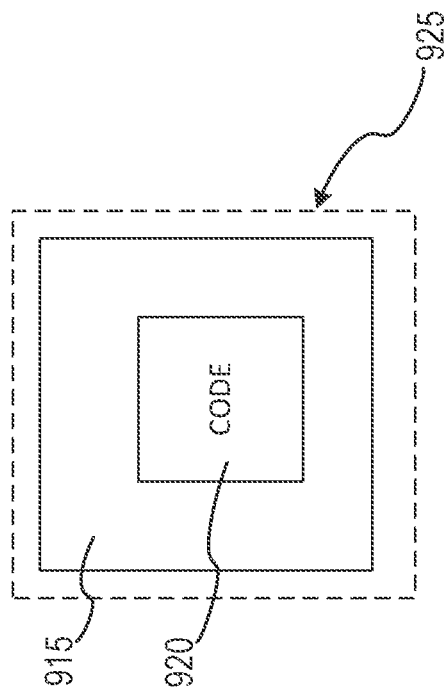
FIGS. 9A and 9B display different modes for generating biological item identifiers, according to some example embodiments.
Figure 9A:
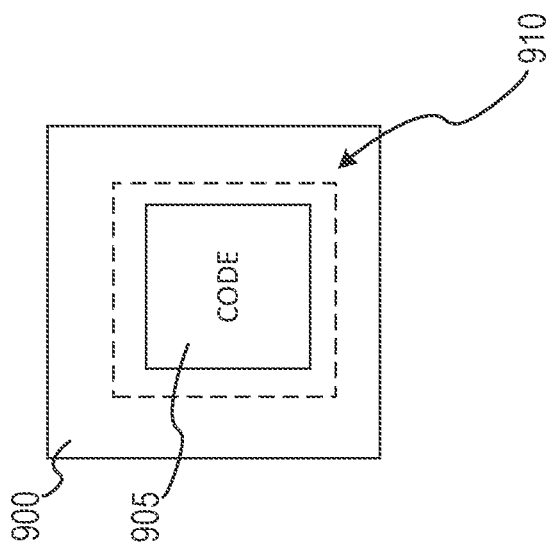

FIGS. 9A and 9B display different modes for generating biological item identifiers, according to some example embodiments. In some example embodiments, the feature engine 505 is configured to detect scannable codes directly as an image feature. For example, with reference to FIG. 9A, the feature engine 505 can implement a convolutional neural network that identifies a scannable code 905 on an item 900 (e.g., a biological container, a vial), and circumscribe the scannable code 905 with a region of interest 910. As discussed below, in some example embodiments, the feature engine 505 uses the region of interest 910 to generate an image tile file or alternatively stores the region of interest 910 with other detected ROIs, which can be input into code engine 510.

In some example embodiments, the feature engine 505 is configured to detect scannable codes indirectly by performing detection of objects other than the scannable code. For example, with reference to FIG. 9B, the feature engine 505 can implement a convolutional neural network that is configured to detect the shape of the item 915 (e.g., a square container, a cylindrical vial) without identifying or otherwise detecting the scannable code 920 included in the item 915. The feature engine 505 can then generate a region of interest 925 which can be used to generate an image file or stored as ROI coordinate data, as discussed above.

Figure 10B:
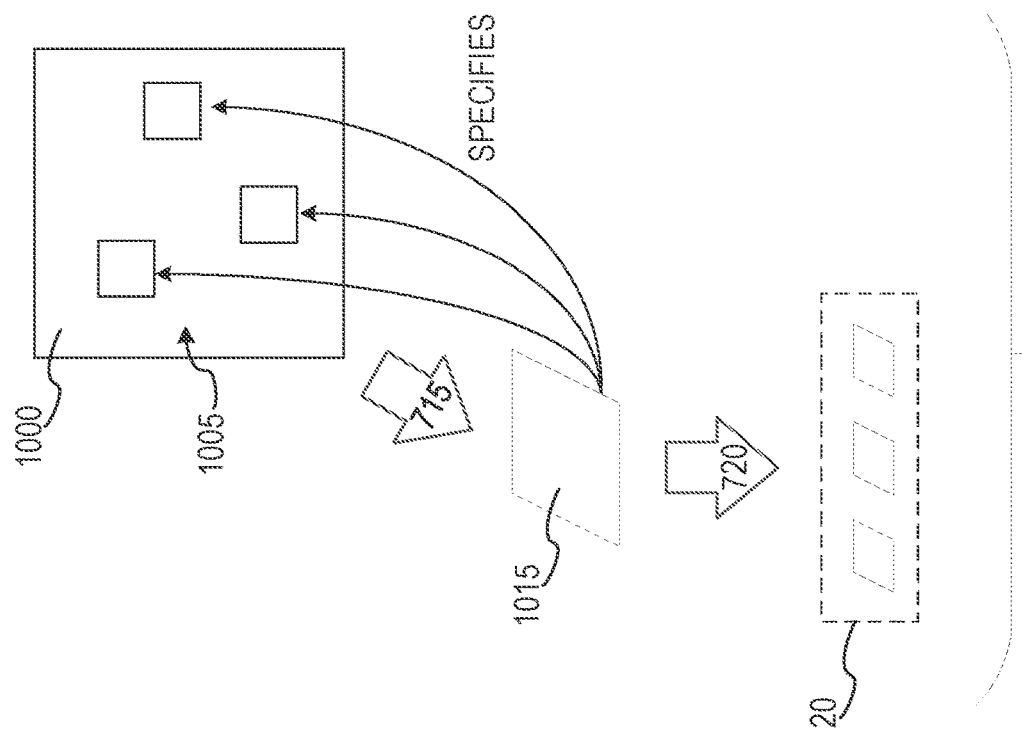
FIGS. 10A and 10B display different modes of generating item identifiers from scannable codes, according to some example embodiments.
Figure 10A:
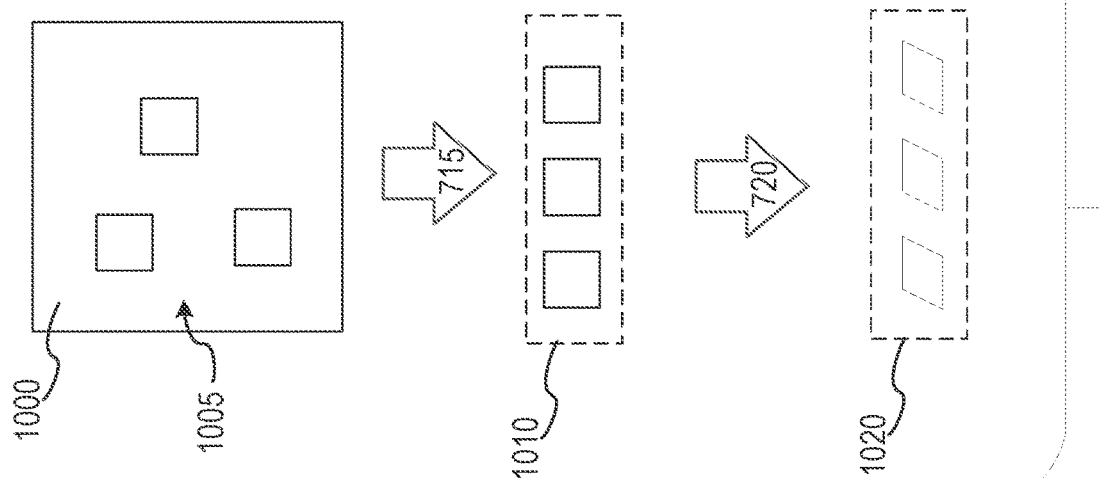

FIGS. 10A and 10B display different modes of generating item identifiers from scannable codes, according to some example embodiments. As discussed above, in some example embodiments, the feature engine 505 generates a plurality of image tiles. For example with reference to FIG. 10A, an image depicts multiple scannable codes 1005, which, at operation 715, are individually cropped to generate a plurality of image tiles 1010. Further, at operation 720, each of the plurality of image tiles 1010 can be processed in a serial operation or parallel operation via code engine 510 to generate a plurality of item identifiers 1020.

Further, according to other example embodiments, the original image is not partitioned into different tiles, but processed directly by directing the code engine 510 to the locations of different scannable codes in the image. For example, with reference to FIG. 10B, the image 1000 depicts a plurality of scannable codes 1005, the locations of which are stored as ROI coordinate data 1015. The ROI coordinate data 1015 comprises ROI coordinates for each of the plurality of scannable codes 1005. For example, ROI coordinate data 1015 includes a first set of coordinates that specify a first of the scannable codes 1005, a second set of coordinates that specify the second of the scannable codes 1005, and a third set of coordinates that specify the third of the scannable codes 1005, and so on. The set of coordinates can be pixel offsets from the borders of the image 1000. For example, a given 40 pixel square ROI can be identified as 200 pixels from the top and 100 pixels from the left side of image 1000. At operation 720, the code engine 510 identifies the ROI coordinate data 1015 and the image 1000, and generates each of the scannable codes directly from the image 1000 in a serial or parallel process, as discussed above.

Figure 11:
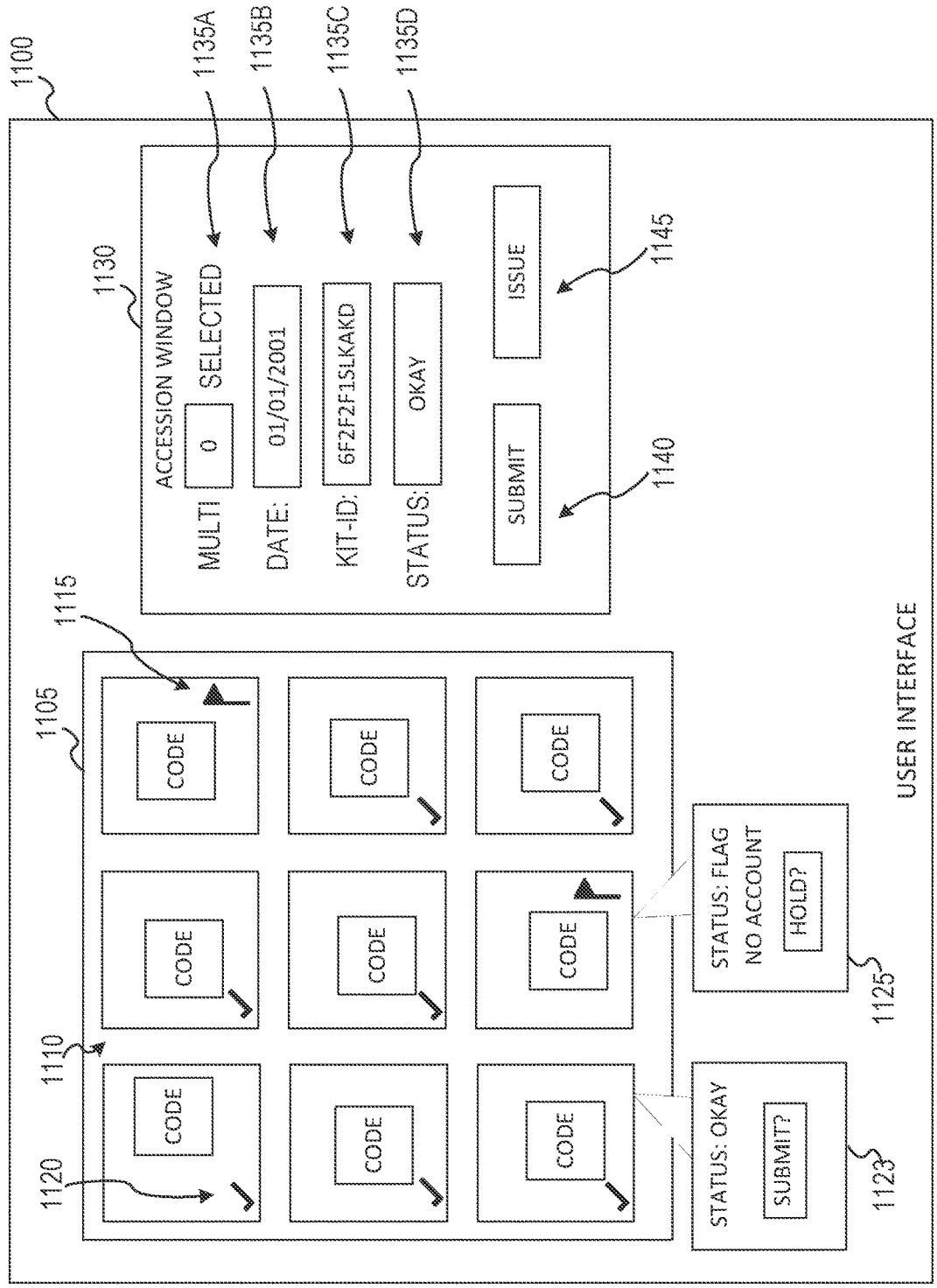
FIG. 11 shows an example user interface, according to some example embodiments.

FIG. 11 shows an example user interface 1100, according to some example embodiments. The user interface 1100 comprises an image 1105 which depicts a plurality of items 1110 as arranged in the original image (e.g., the image generated at operation 705, FIG. 7). The user interface 1100 further displays a plurality of visual indicators that indicate whether each of the depicted items 1110 have scannable codes that correspond to network accounts. For example, visual indicator 1115 is a flag icon that indicates that the depicted biological item (e.g., vial of saliva) has a scannable code that does not have a corresponding network account (e.g., user account in user database 147).

In contrast, visual indicator 1120 is a checkmark that indicates that the depicted biological item does have a corresponding network account. A user viewing user interface 1100 can click or hover over the individual depicted items. For example, by clicking or otherwise selecting the bottom left physical item in the image 1105, interface engine 520 generates window 1123, which displays a status message ("OKAY"), and a UI option (e.g., submit button) to individually record the state of the selected physical item as accessioned in user database 147. As an additional example, by clicking or otherwise selecting the image portion corresponding to the bottom middle biological item, interface engine 520 generates window 1125, which displays a different status message (e.g., "FLAG, NO ACCOUNT"), and a different UI option (e.g., hold button) to individually record the state of the selected biological item is flagged, which can prompt follow-up actions such as a user message via response engine 615.

The user interface 1100 further comprises a form window 1130, with multiple fields 1135A-1135D which may be auto-populated by the interface engine 520 based on data generated from the other engines (e.g., status or results data stored by state engine 515). As illustrated, according to some example embodiments, the user interface 1100 allows a user to efficiently manage multiple biological samples without displaying or otherwise accessing sensitive user data, such as user network account information (e.g., userID), user sequence data, and so on.

The user interface 1100 further comprises submit button 1140 that allows an operator viewing the user interface 1100 to submit data populated in the form window 1130. Further, the user interface 1100 comprises an issue button 1145 that allows an operator to initiate follow-up actions via response engine 615.

FIGS. 12A-15 show example diagrams that correspond to example structural source code included below, according to some example embodiments. The structural source code is an example implementation of the methods discussed above. Comment code is indicated by the use of two forward slashes. One of ordinary skill in the art appreciates that, although the structural source code may resemble a certain programming language, other programming languages can be efficiently used to implement the methods.

Figure 12A:
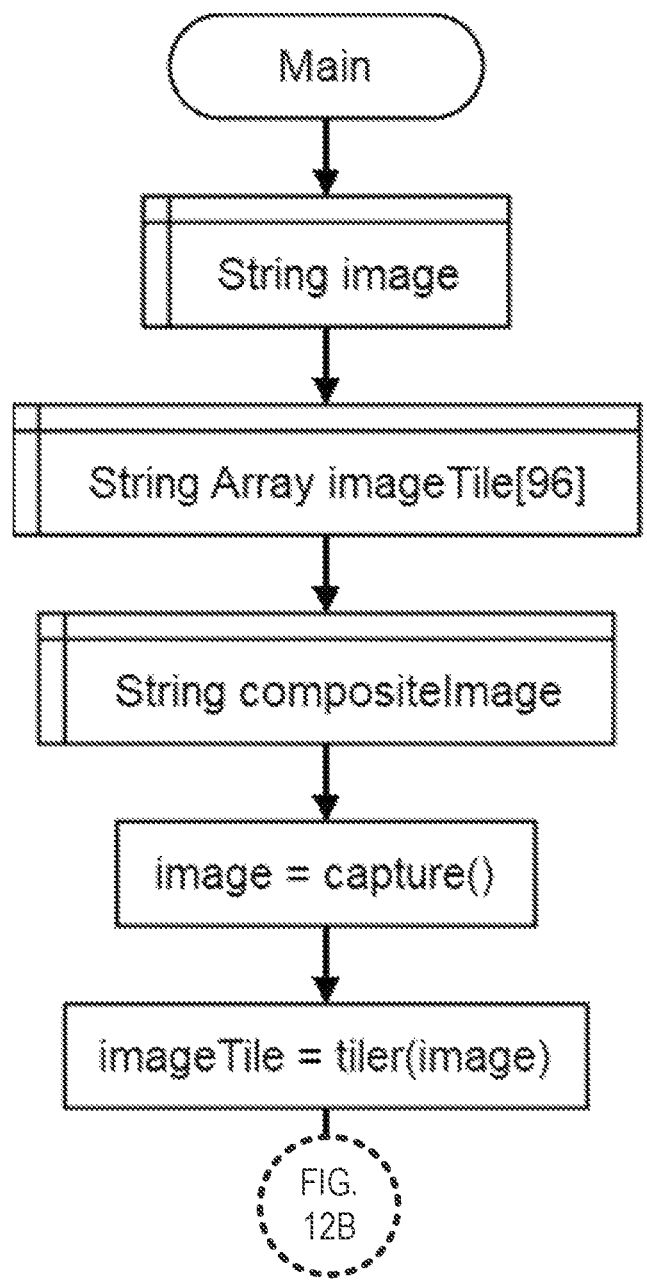
FIGS. 12A-15 show example diagrams that correspond to example structural source code included below, according to some example embodiments.
Figure 12B:
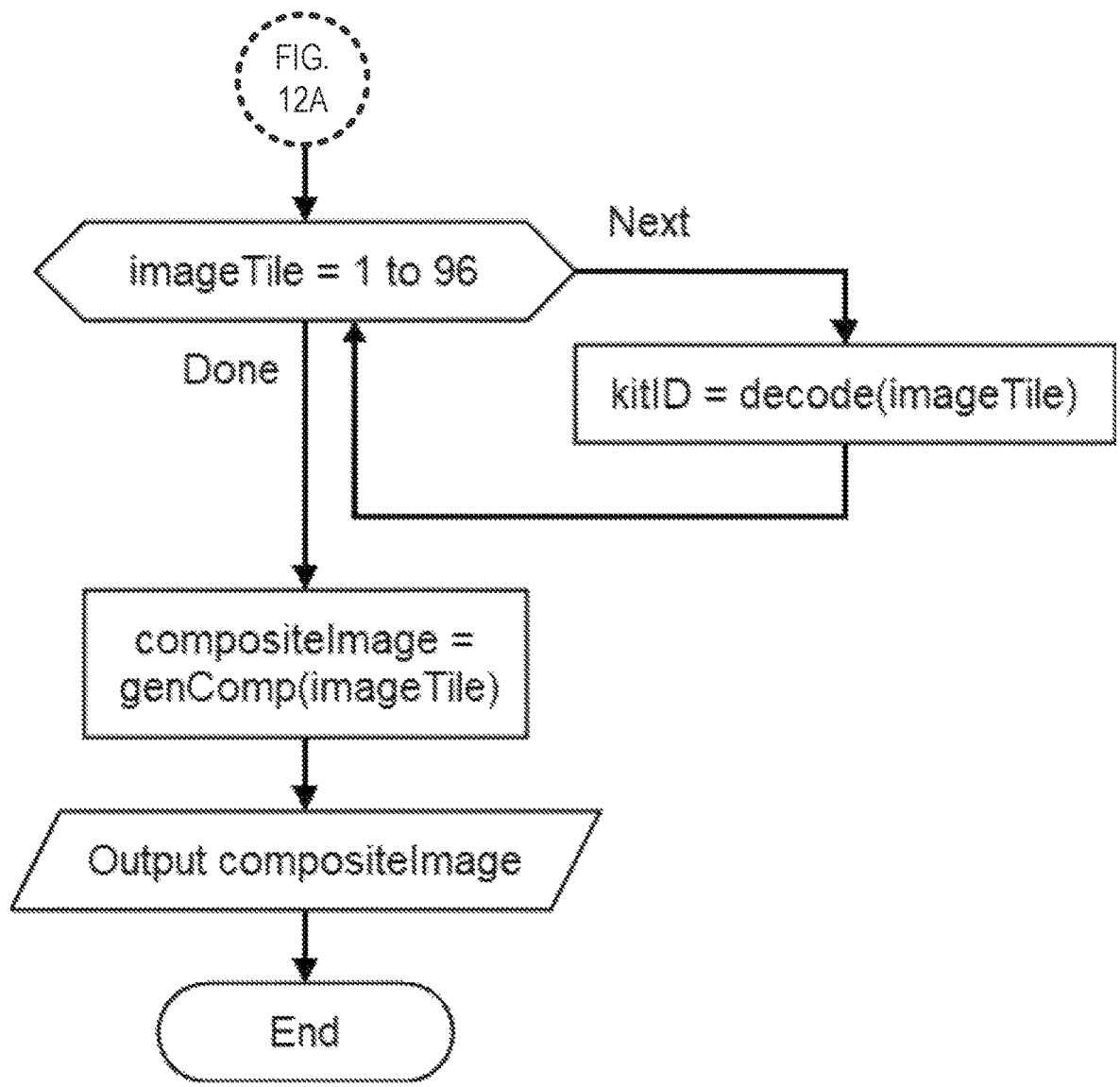
Figure 13:
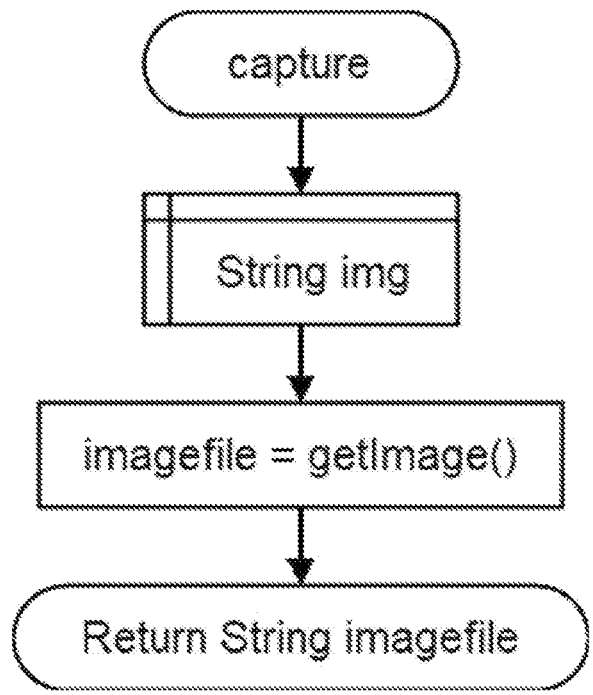
Figure 14:
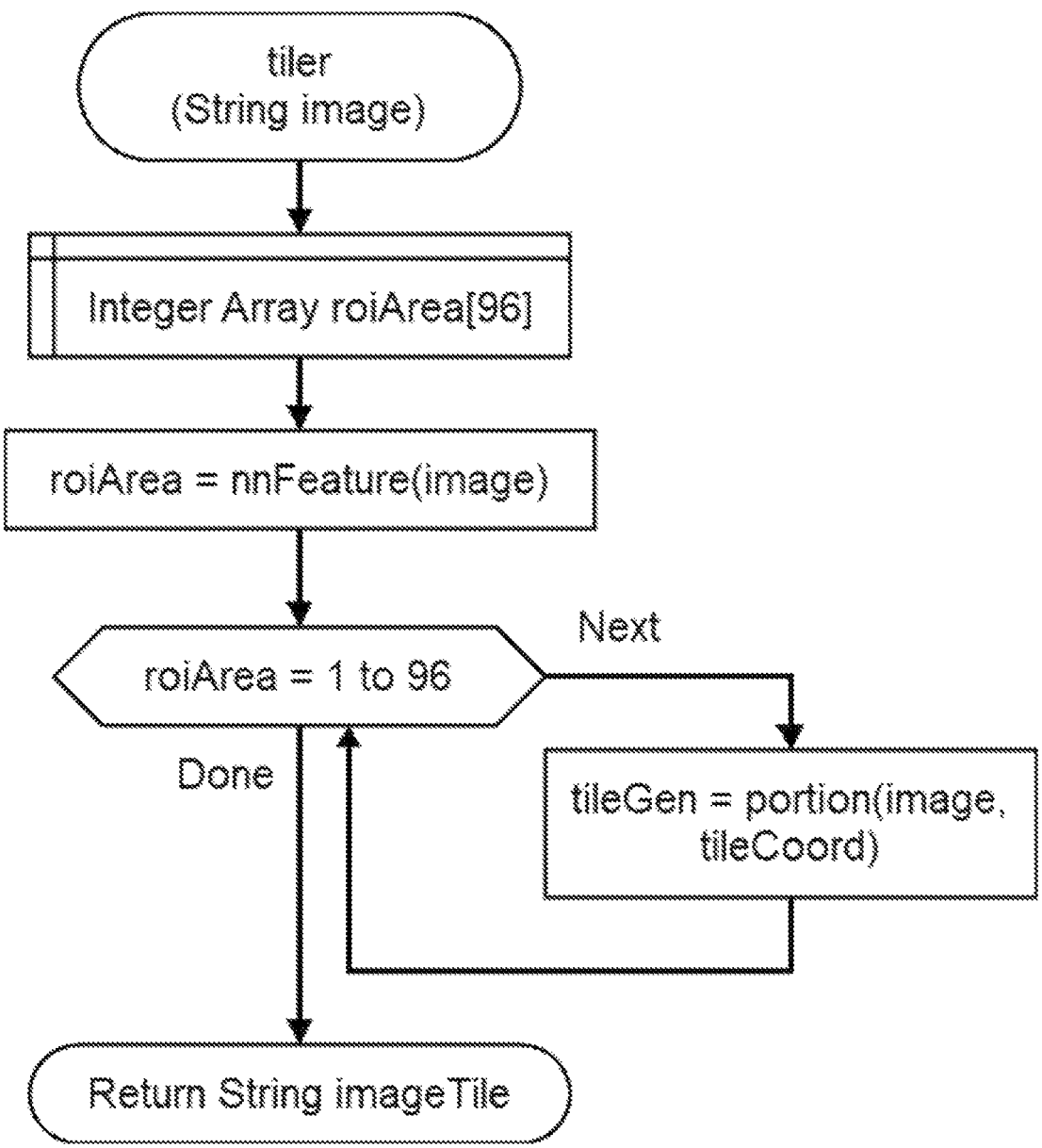
Figure 15:
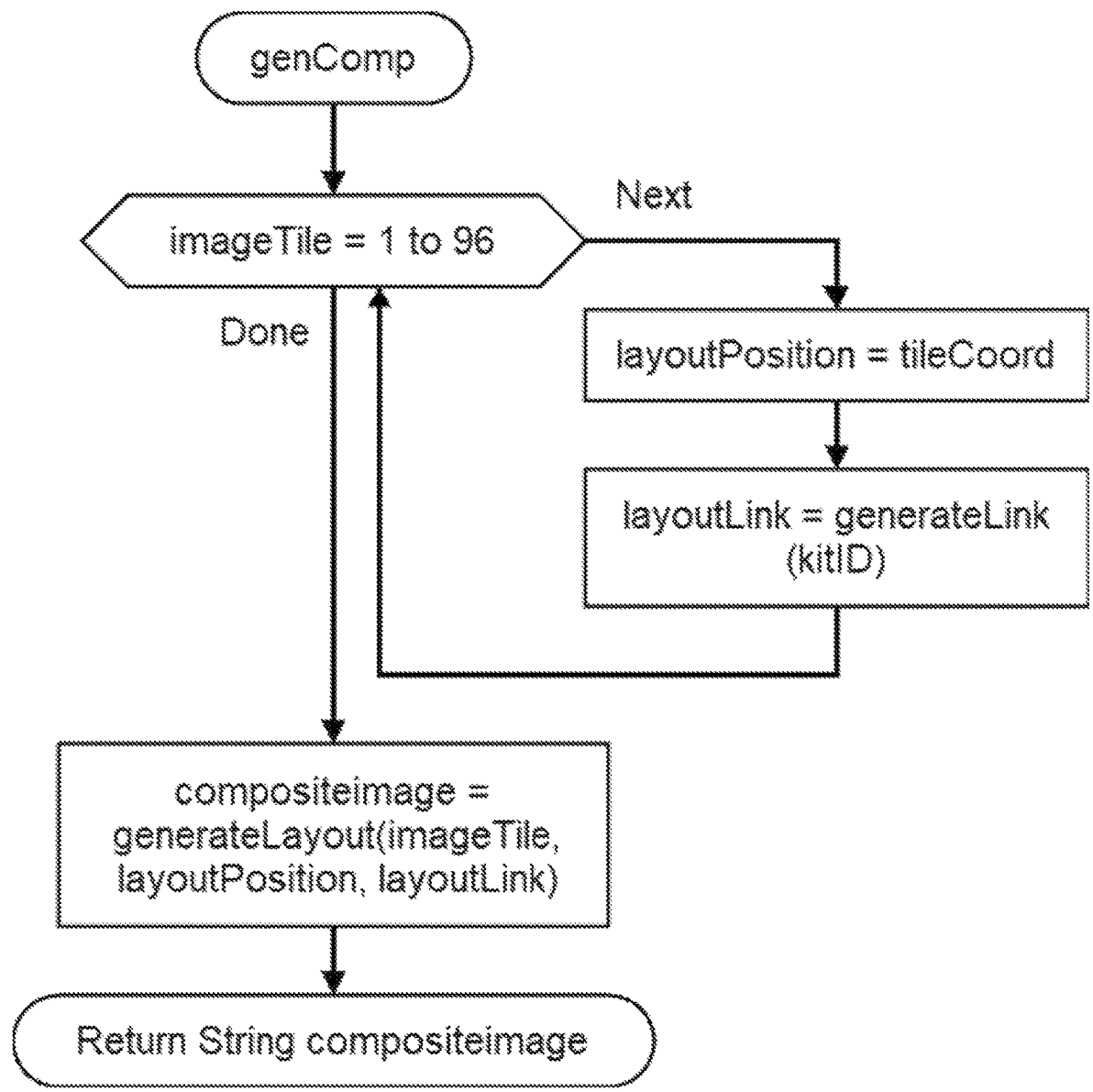

```
BEGIN CODE include <iostream>
include <sstream>
#include <string>
#include <cstdlib>
#include <cmath>
using namespace std;
// Headers
string toString (double);
int toInt (string);
double toDouble (string);
accession();
capture();
genComp();
tiler(image);
//FIG. 12A and 12B
main() {
  // Declare variables.
  string image; //a file name
  string[] imageTile = new string[96];
  string compositeImage;
  // Generate Image
  image = capture();
  // Generate Tiles from Image, each tile comprising a visual code
  imageTile = tiler(image);
  // Decode scannable code to get kitID for each element in imageTile array (an element can be either an individual image tile file or an ROI specifying location of a code in the master image). Output can be an array/set of kitIDs.
  for (imageTile = 1; imageTile <= 96; imageTile++) {
    // decode() can be a barcode or QR code decoder.
    kitID = decode(imageTile);
  }
  states = accession(kitID);
  // Generates composite image that has each tile comprising a bar code, and interactive code (e.g., JavaScript) that pops up a clickable link that auto fills form data on a form configured to submit data to a database.
  compositeImage = genComp(imageTile, states);
  // Display composite image on display device.
  ouput <<compositeImage << endl;
  return 0;
```

```
BEGIN CODE
}
accession() {
  // Received function uploads the kitIDs to the server side.
  received(kitID);
  // Server side logic then matches kitIDs to userIDs. If a kitID has a pre-created userID, the server updates the state column in a state table to 1 to indicate that the user corresponding to the kitID and the userID is accessioned. If the kitID does not have a pre-created userID, the server updates the state column in the kitID table to 0 to indicate that a user is not accessioned (i.e., kitID has been received but no user account has been set up). The state table can include three columns: kitID, state (1 or 0), and date (date state column was updated to 1 or 0).
  // create DB connection
  db = SQLconnect(remotehost);
  // define cursor object
  cursor = connCursor;
  // Query state table for kitID, the state for that kitID, and limit results to those with a submit date that is today's date.
  query = "SELECT kitID, state FROM state WHERE date = CURDATE ()";
  return states;
}
//FIG. 13
capture() {
  img;
  // Generate image file using camera device (the getImage method)
  imagefile = getImage();
  return imagefile;
}
//FIG. 15
genComp() {
  for (imageTile = 1; imageTile <= 96; imageTile++) {
    // For each tile, use that tile's coordinates in the original image to generate a layout position (row, column) in a table to be generated.
    layoutPosition = tileCoord;
    // For each tile, use the kitID previously decoded to generate a network link or application link that form fills kitID data and other data (e.g., vial pass/fail data). The network link can include JavaScript interactive code, such as hover actions.
    lay outLink = generateLink(kitID);
  }
  // The composite image is generated, using the layout position of each tile to place the image file of that tile in the table, and associate the generated link information with the table portion in which the given tile is positioned.
  compositeimage = generateLayout(imageTile, layoutPosition, layoutLink);
  return compositeimage;
}
//FIG. 14
tiler(image) {
  int[] roiArea = new int[96];
  // Apply a convolutional neural network trained to perform object detection of bar codes or other visual codes in the master image. For each visual code detected, draw a bounding box or region of interest (ROI) around detected code. Return roiArea which is an array of ROI coordinates in the master image. Example ROI coordinates can include pixel ranges or offsets within the image to describe the location of the ROI within the image.
  roiArea = nnFeature(image);
  for (roiArea = 1; roiArea <= 96; roiArea++) {
    // For each of the ROIs detected (each element in roiArea array), section off (e.g., crop) the ROI portion from the master image and store as an imageTile file.
    tileGen = portion(image, tileCoord);
  }
  return imageTile;
}
// The following implements type conversion functions.
string toString (double value) { //it also
  stringstream temp;
  temp << value;
  return temp.str();
}
int toInt (string text) {
  return atoi(text.c_str());
}
```

-continued

BEGIN CODE

```
double toDouble (string text) {
    return atof(text.c_str());
}
```

Figure 16:
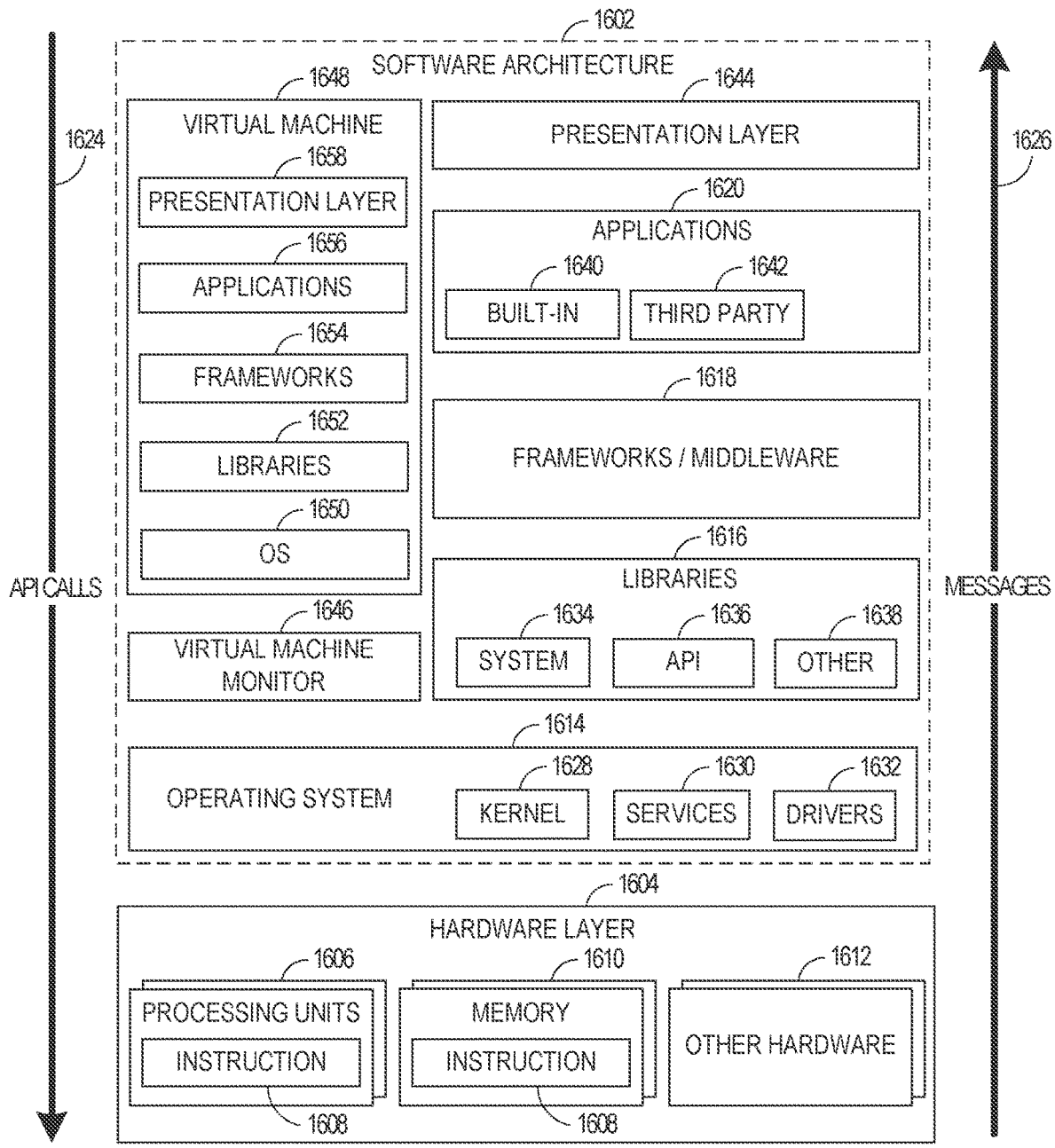
FIG. 16 is a block diagram illustrating an example of a software architecture that may be installed on a machine, according to some example embodiments.

FIG. 16 is a block diagram illustrating an example of a software architecture 1602 that may be installed on a machine, according to some example embodiments. FIG. 16 is merely a non-limiting example of a software architecture, and it will be appreciated that many other architectures may be implemented to facilitate the functionality described herein. The software architecture 1602 may be executing on hardware such as a machine 1700 of FIG. 17 that includes, among other things, processors 1710, memory 1730, and I/O components 1750. A representative hardware layer 1604 is illustrated and can represent, for example, the machine 1700 of FIG. 17. The representative hardware layer 1604 comprises one or more processing units 1606 having associated executable instructions 1608. The executable instructions 1608 represent the executable instructions of the software architecture 1602, including implementation of the methods, modules, and so forth of the above figures. The hardware layer 1604 also includes memory or storage modules 1610, which also have the executable instructions 1608. The hardware layer 1604 may also comprise other hardware 1612, which represents any other hardware of the hardware layer 1604, such as the other hardware illustrated as part of the machine 1600.

In the example architecture of FIG. 16, the software architecture 1602 may be conceptualized as a stack of layers, where each layer provides particular functionality. For example, the software architecture 1602 may include layers such as an operating system 1614, libraries 1616, frameworks/middleware 1618, applications 1620, and a presentation layer 1644. Operationally, the applications 1620 or other components within the layers may invoke API calls 1624 through the software stack and receive a response, returned values, and so forth (illustrated as messages 1626) in response to the API calls 1624. The layers illustrated are representative in nature, and not all software architectures have all layers. For example, some mobile or special purpose operating systems may not provide a frameworks/middleware 1618 layer, while others may provide such a layer. Other software architectures may include additional or different layers.

The operating system 1614 may manage hardware resources and provide common services. The operating system 1614 may include, for example, a kernel 1628, services 1630, and drivers 1632. The kernel 1628 may act as an abstraction layer between the hardware and the other software layers. For example, the kernel 1628 may be responsible for memory management, processor management (e.g., scheduling), component management, networking, security settings, and so on. The services 1630 may provide other common services for the other software layers. The drivers 1632 may be responsible for controlling or interfacing with the underlying hardware. For instance, the drivers 1632 may include display drivers, camera drivers, Bluetooth® drivers, flash memory drivers, serial communication drivers (e.g., Universal Serial Bus (USB) drivers), Wi-Fi® drivers, audio drivers, power management drivers, and so forth depending on the hardware configuration.

The libraries 1616 may provide a common infrastructure that may be utilized by the applications 1620 and/or other components and/or layers. The libraries 1616 typically provide functionality that allows other software modules to perform tasks in an easier fashion than by interfacing directly with the underlying operating system 1614 functionality (e.g., kernel 1628, services 1630, or drivers 1632). The libraries 1616 may include system libraries 1634 (e.g., C standard library) that may provide functions such as memory allocation functions, string manipulation functions, mathematic functions, and the like. In addition, the libraries 1616 may include API libraries 1636 such as media libraries (e.g., libraries to support presentation and manipulation of various media formats such as MPEG4, H.264, MP3, AAC, AMR, JPG, PNG), graphics libraries (e.g., an OpenGL framework that may be used to render 2D and 3D graphic content on a display), database libraries (e.g., SQLite that may provide various relational database functions), web libraries (e.g., WebKit that may provide web browsing functionality), and the like. The libraries 1616 may also include a wide variety of other libraries 1638 to provide many other APIs to the applications 1620 and other software components/modules.

The frameworks 1618 (also sometimes referred to as middleware) may provide a higher-level common infrastructure that may be utilized by the applications 1620 or other software components/modules. For example, the frameworks/middleware 1618 may provide various graphic user interface (GUI) functions, high-level resource management, high-level location services, and so forth. The frameworks/middleware 1618 may provide a broad spectrum of other APIs that may be utilized by the applications 1620 and/or other software components/modules, some of which may be specific to a particular operating system or platform.

The applications 1620 include built-in applications 1640 and/or third-party applications 1642. Examples of representative built-in applications 1640 may include, but are not limited to, a home application, a contacts application, a browser application, a book reader application, a location application, a media application, a messaging application, or a game application.

The third-party applications 1642 may include any of the built-in applications 1640, as well as a broad assortment of other applications. In a specific example, the third-party applications 1642 (e.g., an application developed using the Android™ or iOS™ software development kit (SDK) by an entity other than the vendor of the particular platform) may be mobile software running on a mobile operating system such as iOS™, Android™, Windows® Phone, or other mobile operating systems. In this example, the third-party applications 1642 may invoke the API calls 1624 provided by the mobile operating system such as the operating system 1614 to facilitate functionality described herein.

The applications 1620 may utilize built-in operating system functions (e.g., kernel 1628, services 1630, or drivers 1632), libraries (e.g., system libraries 1634, API libraries 1636, and other libraries 1638), or frameworks/middleware 1618 to create user interfaces to interact with users of the system. Alternatively, or additionally, in some systems, interactions with a user may occur through a presentation layer, such as the presentation layer 1644. In these systems, the application/module "logic" can be separated from the aspects of the application/module that interact with the user.

Some software architectures utilize virtual machines. In the example of FIG. 16, this is illustrated by a virtual machine 1648. A virtual machine creates a software environment where applications/modules can execute as if they were executing on a hardware machine e.g., the machine 1700 of FIG. 17, for example). A virtual machine 1648 is hosted by a host operating system (e.g., operating system 1614) and typically, although not always, has a virtual machine monitor 1646, which manages the operation of the virtual machine 1648 as well as the interface with the host operating system (e.g., operating system 1614). A software architecture executes within the virtual machine 1648, such as an operating system 1650, libraries 1652, frameworks/middleware 1654, applications 1656, or a presentation layer 1658. These layers of software architecture executing within the virtual machine 1648 can be the same as corresponding layers previously described or may be different.

Figure 17:
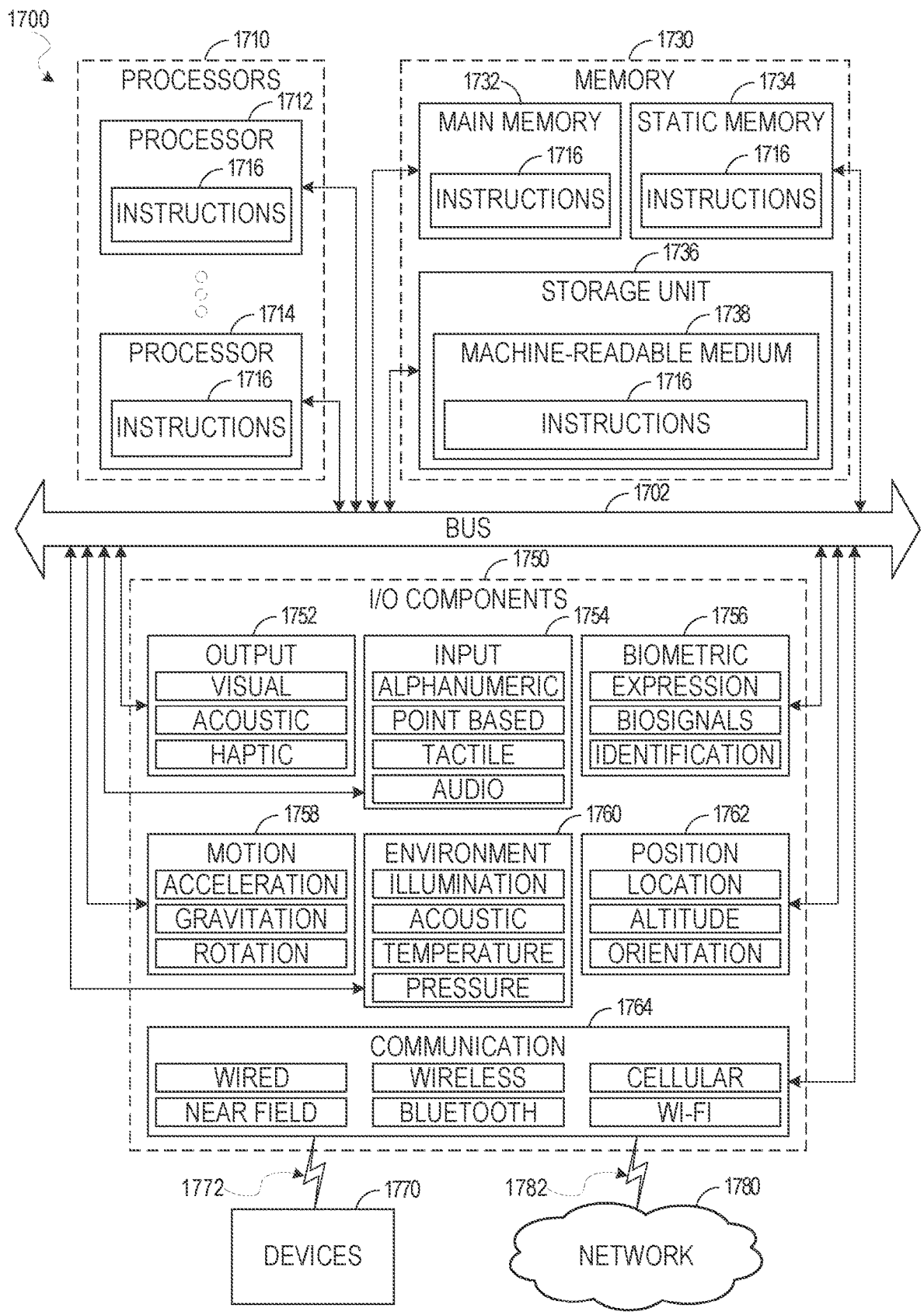
FIG. 17 illustrates a diagrammatic representation of a machine in the form of a computer system within which a set of instructions may be executed for causing the machine to perform any one or more of the methodologies discussed herein, according to an example embodiment.

FIG. 17 illustrates a diagrammatic representation of a machine 1700 in the form of a computer system within which a set of instructions may be executed for causing the machine to perform any one or more of the methodologies discussed herein, according to an example embodiment. Specifically, FIG. 17 shows a diagrammatic representation of the machine 1700 in the example form of a computer system, within which instructions 1716 (e.g., software, a program, an application, an applet, an app, or other executable code) for causing the machine 1700 to perform any one or more of the methodologies discussed herein may be executed. For example, the instructions 1716 may cause the machine 1700 to execute the above methods. The instructions 1716 transform the general, non-programmed machine 1700 into a particular machine 1700 programmed to carry out the described and illustrated functions in the manner described. In alternative embodiments, the machine 1700 operates as a standalone device or may be coupled (e.g., networked) to other machines. In a networked deployment, the machine 1700 may operate in the capacity of a server machine or a client machine in a server-client network environment, or as a peer machine in a peer-to-peer (or distributed) network environment. The machine 1700 may comprise, but not be limited to, a server computer, a client computer, a personal computer (PC), a tablet computer, a laptop computer, a netbook, a set-top box (STB), a PDA, an entertainment media system, a cellular telephone, a smart phone, a mobile device, a wearable device (e.g., a smart watch), a smart home device (e.g., a smart appliance), other smart devices, a web appliance, a network root, a network switch, a network bridge, or any machine capable of executing the instructions 1716, sequentially or otherwise, that specify actions to be taken by the machine 1700. Further, while only a single machine 1700 is illustrated, the term "machine" shall also be taken to include a collection of machines 1700 that individually or jointly execute the instructions 1716 to perform any one or more of the methodologies discussed herein.

The machine 1700 may include processors 1710, memory 1730, and I/O components 1750, which may be configured to communicate with each other such as via a bus 1702. In an example embodiment, the processors 1710 (e.g., a Central Processing Unit (CPU), a Reduced Instruction Set Computing (RISC) processor, a Complex Instruction Set Computing (CISC) processor, a Graphics Processing Unit (GPU), a Digital Signal Processor (DSP), an ASIC, a Radio-Frequency Integrated Circuit (RFIC), another processor, or any suitable combination thereof) may include, for example, a processor 1712 and a processor 1714 that may execute the instructions 1716. The term "processor" is intended to include multi-core processors that may comprise two or more independent processors (sometimes referred to as "cores") that may execute instructions contemporaneously. Although FIG. 17 shows multiple processors 1710, the machine 1700 may include a single processor with a single core, a single processor with multiple cores (e.g., a multi-core processor), multiple processors with a single core, multiple processors with multiples cores, or any combination thereof.

The memory 1730 may include a main memory 1732, a static memory 1734, and a storage unit 1736, both accessible to the processors 1710 such as via the bus 1702. The main memory 1732, the static memory 1734, and storage unit 1736 store the instructions 1716 embodying any one or more of the methodologies or functions described herein. The instructions 1716 may also reside, completely or partially, within the main memory 1732, within the static memory 1734, within the storage unit 1736, within at least one of the processors 1710 (e.g., within the processor's cache memory), or any suitable combination thereof, during execution thereof by the machine 1700.

The I/O components 1750 may include a wide variety of components to receive input, provide output, produce output, transmit information, exchange information, capture measurements, and so on. The specific I/O components 1750 that are included in a particular machine will depend on the type of machine. For example, portable machines such as mobile phones will likely include a touch input device or other such input mechanisms, while a headless server machine will likely not include such a touch input device. It will be appreciated that the I/O components 1750 may include many other components that are not shown in FIG. 17. The I/O components 1750 are grouped according to functionality merely for simplifying the following discussion and the grouping is in no way limiting. In various example embodiments, the I/O components 1750 may include output components 1752 and input components 1754. The output components 1752 may include visual components (e.g., a display such as a plasma display panel (PDP), a light emitting diode (LED) display, a liquid crystal display (LCD), a projector, or a cathode ray tube (CRT)), acoustic components (e.g., speakers), haptic components (e.g., a vibratory motor, resistance mechanisms), other signal generators, and so forth. The input components 1754 may include alphanumeric input components (e.g., a keyboard, a touch screen configured to receive alphanumeric input, a photo-optical keyboard, or other alphanumeric input components), point-based input components (e.g., a mouse, a touchpad, a trackball, a joystick, a motion sensor, or another pointing instrument), tactile input components (e.g., a physical button, a touch screen that provides location and/or force of touches or touch gestures, or other tactile input components), audio input components (e.g., a microphone), and the like.

In further example embodiments, the I/O components 1750 may include biometric components 1756, motion components 1758, environmental components 1760, or position components 1762, among a wide array of other components. For example, the biometric components 1756 may include components to detect expressions (e.g., hand expressions, facial expressions, vocal expressions, body gestures, or eye tracking), measure biosignals (e.g., blood pressure, heart rate, body temperature, perspiration, or brain waves), identify a person (e.g., voice identification, retinal identification, facial identification, fingerprint identification, or electroencephalogram-based identification), and the like. The motion components 1758 may include acceleration sensor components (e.g., accelerometer), gravitation sensor components, rotation sensor components (e.g., gyroscope), and so forth. The environmental components 1760 may include, for example, illumination sensor components (e.g., photometer), temperature sensor components (e.g., one or more thermometers that detect ambient temperature), humidity sensor components, pressure sensor components (e.g., barometer), acoustic sensor components (e.g., one or more microphones that detect background noise), proximity sensor components (e.g., infrared sensors that detect nearby objects), gas sensors (e.g., gas detection sensors to detection concentrations of hazardous gases for safety or to measure pollutants in the atmosphere), or other components that may provide indications, measurements, or signals corresponding to a surrounding physical environment. The position components 1762 may include location sensor components (e.g., a GPS receiver component), altitude sensor components (e.g., altimeters or barometers that detect air pressure from which altitude may be derived), orientation sensor components (e.g., magnetometers), and the like.

Communication may be implemented using a wide variety of technologies. The I/O components 1750 may include communication components 1764 operable to couple the machine 1700 to a network 1780 or devices 1770 via a coupling 1782 and a coupling 1772, respectively. For example, the communication components 1764 may include a network interface component or another suitable device to interface with the network 1780. In further examples, the communication components 1764 may include wired communication components, wireless communication components, cellular communication components, Near Field Communication (NFC) components, Bluetooth® components (e.g., Bluetooth® Low Energy), Wi-Fi® components, and other communication components to provide communication via other modalities. The devices 1770 may be another machine or any of a wide variety of peripheral devices (e.g., a peripheral device coupled via a USB).

Moreover, the communication components 1764 may detect identifiers or include components operable to detect identifiers. For example, the communication components 1764 may include Radio Frequency Identification (RFID) tag reader components, NFC smart tag detection components, optical reader components (e.g., an optical sensor to detect one-dimensional bar codes such as Universal Product Code (UPC) bar code, multi-dimensional bar codes such as Quick Response (QR) code, Aztec code, Data Matrix, Dataglyph, MaxiCode, PDF417, Ultra Code, UCC RSS-2D bar code, and other optical codes), or acoustic detection components (e.g., microphones to identify tagged audio signals). In addition, a variety of information may be derived via the communication components 1764, such as location via Internet Protocol (IP) geolocation, location via Wi-Fi® signal triangulation, location via detecting an NFC beacon signal that may indicate a particular location, and so forth.

The various memories (i.e., 1730, 1732, 1734, and/or memory of the processor(s) 1710) and/or storage unit 1736 may store one or more sets of instructions and data structures (e.g., software) on an a readable medium (e.g., machine-readable medium 1738) embodying or utilized by any one or more of the methodologies or functions described herein. These instructions (e.g., the instructions 1716), when executed by processor(s) 1710, cause various operations to implement the disclosed embodiments.

As used herein, the terms "machine-storage medium," "device-storage medium," "computer-storage medium" mean the same thing and may be used interchangeably in this disclosure. The terms refer to a single or multiple storage devices and/or media (e.g., a centralized or distributed database, and/or associated caches and servers) that store executable instructions and/or data. The terms shall accordingly be taken to include, but not be limited to, solid-state memories, and optical and magnetic media, including memory internal or external to processors. Specific examples of machine-storage media, computer-storage media and/or device-storage media include non-volatile memory, including by way of example semiconductor memory devices, e.g., erasable programmable read-only memory (EPROM), electrically erasable programmable read-only memory (EEPROM), FPGA, and flash memory devices; magnetic disks such as internal hard disks and removable disks; magneto-optical disks; and CD-ROM and DVD-ROM disks. The terms "machine-storage media," "computer-storage media," and "device-storage media" specifically exclude carrier waves, modulated data signals, and other such media, at least some of which are covered under the term "signal medium" discussed below.

In various example embodiments, one or more portions of the network 1780 may be an ad hoc network, an intranet, an extranet, a VPN, a LAN, a WLAN, a WAN, a WWAN, a MAN, the Internet, a portion of the Internet, a portion of the PSTN, a plain old telephone service (POTS) network, a cellular telephone network, a wireless network, a Wi-Fi® network, another type of network, or a combination of two or more such networks. For example, the network 1780 or a portion of the network 1780 may include a wireless or cellular network, and the coupling 1782 may be a Code Division Multiple Access (CDMA) connection, a Global System for Mobile communications (GSM) connection, or another type of cellular or wireless coupling. In this example, the coupling 1782 may implement any of a variety of types of data transfer technology, such as Single Carrier Radio Transmission Technology (1×RTT), Evolution-Data Optimized (EVDO) technology, General Packet Radio Service (GPRS) technology, Enhanced Data rates for GSM Evolution (EDGE) technology, third Generation Partnership Project (3GPP) including 3G, fourth generation wireless (4G) networks, Universal Mobile Telecommunications System (UMTS), High Speed Packet Access (HSPA), Worldwide Interoperability for Microwave Access (WiMAX), Long Term Evolution (LTE) standard, others defined by various standard-setting organizations, other long range protocols, or other data transfer technology.

The instructions 1716 may be transmitted or received over the network 1780 using a transmission medium via a network interface device (e.g., a network interface component included in the communication components 1764) and utilizing any one of a number of well-known transfer protocols (e.g., hypertext transfer protocol (HTTP)). Similarly, the instructions 1716 may be transmitted or received using a transmission medium via the coupling 1772 (e.g., a peer-to-peer coupling) to the devices 1770. The terms "transmission medium" and "signal medium" mean the same thing and may be used interchangeably in this disclosure. The terms "transmission medium" and "signal medium" shall be taken to include any intangible medium that is capable of storing, encoding, or carrying the instructions 1716 for execution by the machine 1700, and includes digital or analog communications signals or other intangible media to facilitate communication of such software. Hence, the terms "transmission medium" and "signal medium" shall be taken to include any form of modulated data signal, carrier wave, and so forth. The term "modulated data signal" means a signal that has one or more of its characteristics set or changed in such a matter as to encode information in the signal.

What is claimed is:

1. A method comprising:
    identifying an image of a plurality of physical items having scannable codes;
    generating a plurality of physical item identifiers from the scannable codes in the image;
    determining, via one or more requests to a remote networked device, that one or more of the plurality of physical item identifiers correspond to no user accounts on the remote networked device and that other physical item identifiers of the plurality of physical item identifiers correspond to user accounts on the remote networked device;
    generating a user interface with visual elements that include a first visual element indicating that a first physical item depicted in the image has a first scannable code that corresponds to a user account on the remote networked device, the visual elements further including a second visual element indicating that a second physical item depicted in the image has a second scannable code that corresponds to no user account on the remote networked device; and
    causing, by a processor of a user device, presentation of the user interface.

2. The method of claim 1, wherein the generated user interface depicts the scannable codes, and each scannable code in the user interface is selectable to access data about a physical item identifier corresponding to the scannable code.

3. The method of claim 2, further comprising:
    receiving, through the user interface, one or more selections of the scannable codes in the user interface that do not have a corresponding network account on the remote networked device; and
    storing, in a database, a flag status for each of the one or more selected scannable codes, the flag status indicating that corresponding network accounts do not exist for the physical item identifiers of the selected scannable codes.

4. The method of claim 1, further comprising:
    automatically uploading batch data indicating one or more physical item identifiers that have network accounts on the remote networked device.

5. The method of claim 4, wherein the batch data comprises physical item identifiers and metadata indicating which of the physical item identifiers have corresponding network accounts.

6. The method of claim 2, wherein the data accessed about the physical item identifier comprises a network link configured to populate one or more fields in the user interface, the one or more fields comprising a physical item identifier field.

7. The method of claim 1, wherein the user accounts have user account identifiers, and wherein the user interface does not display the user account identifiers.

8. The method of claim 1, further comprising:
    transmitting the one or more requests to the remote networked device, the one or more requests comprising one or more of the plurality of physical item identifiers; and
    receiving, from the remote networked device, a response indicating that one or more physical item identifiers do not have corresponding user accounts.

9. The method of claim 1, wherein generating the plurality of physical item identifiers comprises identifying, in the image, regions of interest (ROIs) using a convolutional neural network, each of the ROIs having image coordinates within the image.

10. The method of claim 9, wherein generating the plurality of physical item identifiers comprises:
    specifying, for each ROI, the image coordinates of the ROI in the image; and
    decoding a scannable code from the image using the image coordinates of the ROI.

11. The method of claim 9, wherein generating the plurality of physical item identifiers comprises:
    generating a plurality of image portion files by cropping each of the ROIs; and
    individually decoding a scannable code from each of the image portion files.

12. The method of claim 1, wherein the physical items are biological sample containers.

13. A system comprising:
    one or more processors of a client device; and
    a memory storing instructions that, when executed by the one or more processors, cause the system to perform operations comprising:
        identifying an image of a plurality of physical items having scannable codes;
        generating a plurality of physical item identifiers from the scannable codes in the image;
        determining, via one or more requests to a remote networked device that one or more of the plurality of physical item identifiers correspond to no user accounts on the remote networked device and that other physical item identifiers of the plurality of physical item identifiers correspond to user accounts on the remote networked device;
        generating a user interface with visual elements that include a first visual element indicating that a first physical item depicted in the image has a first scannable code that corresponds to a user account on the remote networked device, the visual elements further including a second visual element indicating that a second physical item depicted in the image has a second scannable code that corresponds to no user account on the remote networked device indicate one or more of the plurality corresponding user accounts on the remote networked device, without displaying user account data for the physical item identifiers having existing user accounts; and
        causing, by a processor of a user device, presentation of the user interface.

14. The system of claim 13, wherein the generated user interface depicts the scannable codes, and each scannable code in the user interface is selectable to access data about a physical item identifier corresponding to the scannable code.

15. The system of claim 14, the operations further comprising:
    receiving, through the user interface, one or more selections of the scannable codes in the user interface that do not have a corresponding network account on the remote networked device; and
    storing, in a database, a flag status for each of the one or more selected scannable codes, the flag status indicating that corresponding network accounts do not exist for the physical item identifiers of the selected scannable codes.

16. The system of claim 13, the operations further comprising:
in response to determining whether each of the plurality of physical item identifiers has a network account identifier that is not accessible on the client device, automatically batch uploading a success status for physical item identifiers that do have network accounts on the remote networked device.

17. The system of claim 13, wherein generating the plurality of physical item identifiers comprises:
generating a plurality of image portion files by cropping each of multiple regions of interest (ROIs); and
individually decoding a scannable code from each of the image portion files.

18. The system of claim 14, wherein the data accessed about the physical item identifier comprises a network link configured to populate one or more fields in the user interface, the one or more fields comprising a physical item identifier field.

19. The system of claim 13, wherein the user accounts have user account identifiers, and wherein the user interface does not display the user account identifiers.

20. A machine-readable storage device embodying instructions that, when executed by a device, cause the device to perform operations comprising:
identifying an image of a plurality of physical items having scannable codes;
generating a plurality of physical item identifiers from the scannable codes in the image;
determining, via one or more requests to a remote networked device that one or more of the plurality of physical item identifiers correspond to no user accounts on the remote networked device and that other physical item identifiers of the plurality of physical item identifiers correspond to user accounts on the remote networked device;
generating a user interface with one or more visual elements that include a first visual element indicating that a first physical item depicted in the image has a first scannable code that corresponds to a user account on the remote networked device, the visual elements further including a second visual element indicating that a second physical item depicted in the image has a second scannable code that corresponds to no user account on the remote networked device; and
causing, by a processor of a user device, presentation of the user interface.

\* \* \* \* \*

UNITED STATES PATENT AND TRADEMARK OFFICE
CERTIFICATE OF CORRECTION

PATENT NO. : 11,676,020 B2
APPLICATION NO. : 17/678733
DATED : June 13, 2023
INVENTOR(S) : Li et al.

It is certified that error appears in the above-identified patent and that said Letters Patent is hereby corrected as shown below:

On the Title Page

On page 2, in Column 2, under Item (56), Line 1, delete "2013/0001741 A1" and insert --2013/0174100 A1-- therefor In the Specification In Column 4, Line 19, delete "genomics" and insert --genomic-- therefor In Column 15, Line 36, delete "genomics" and insert --genomic-- therefor In Column 18, Lines 7-8, delete "pre- created" and insert --pre-created-- therefor In Column 18, Line 36, delete "lay outLink" and insert --layoutLink-- therefor In Column 18, Lines 40-41, delete "layout- Link);" and insert --layoutLink);-- therefor In the Claims In Column 26, Lines 44-48, in Claim 13, delete "device indicate one or more of the plurality corresponding user accounts on the remote networked device, without displaying user account data for the physical item identifiers having existing user accounts; and" and insert --device; and-- therefor Signed and Sealed this
Fifteenth Day of October, 2024

Katherine Kelly Vidal
*Director of the United States Patent and Trademark Office*